US012127956B2

(12) United States Patent
Parodi

(10) Patent No.: US 12,127,956 B2
(45) Date of Patent: Oct. 29, 2024

(54) UNIVERSAL ENDOVASCULAR GRAFTS

(71) Applicant: Bolton Medical, Inc., Sunrise, FL (US)

(72) Inventor: Juan Carlos Parodi, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 0 days.

(21) Appl. No.: 17/900,355

(22) Filed: Aug. 31, 2022

(65) Prior Publication Data

US 2023/0102994 A1    Mar. 30, 2023

Related U.S. Application Data

(63) Continuation of application No. 14/272,818, filed on May 8, 2014, now Pat. No. 11,446,167, which is a (Continued)

(51) Int. Cl.
*A61F 2/07* (2013.01)
*A61F 2/06* (2013.01)
(Continued)

(52) U.S. Cl.
CPC ............. *A61F 2/856* (2013.01); *A61F 2/06* (2013.01); *A61F 2/07* (2013.01);
(Continued)

(58) Field of Classification Search
None
See application file for complete search history.

(56) References Cited

U.S. PATENT DOCUMENTS

| 4,501,263 A | 2/1985 | Harbuck |
| 5,123,917 A | 6/1992 | Lee |

(Continued)

FOREIGN PATENT DOCUMENTS

| CN | 201230914 Y | 5/2009 |
| CN | 101601618 A | 12/2009 |

(Continued)

OTHER PUBLICATIONS

"Bolton Medical Thoracic Branch Graft Case Presentation," Charing Cross Symposium Annual Meeting, London, Apr. 8-12, 2011.
(Continued)

*Primary Examiner* — Ann Schillinger
(74) *Attorney, Agent, or Firm* — Foley Hoag LLP; Stephen J. Kenny

(57) ABSTRACT

Universal endovascular grafts are provided for evaluation and repair of damaged or aneurismal blood vessels. More particularly, the present invention relates to universal fenestrated and universal branched endografts for repair of blood vessels with branches, methods for implanting the endografts in the vessel and for making connection with one or more branches. The universal fenestrated endografts have a body with a first end, a second end, a first wall, a second wall, and an interior passage or lumen. The body further includes openings in communication with the passage at the first and second ends and one or more lateral fenestrations in communication with the lumen. The body further has a necked portion between the ends and a cannulation member. The universal branched endografts have a tubular body with a main lumen and four branch lumens. A large branch extends from the body. The four lumens are positioned about a circumference of the tubular body.

16 Claims, 17 Drawing Sheets

Related U.S. Application Data continuation of application No. PCT/US2012/064612, filed on Nov. 12, 2012.

(60) Provisional application No. 61/559,016, filed on Nov. 11, 2011, provisional application No. 61/559,021, filed on Nov. 11, 2011.

(51) Int. Cl.
*A61F 2/856* (2013.01)
*A61F 2/89* (2013.01)

(52) U.S. Cl.
CPC ......... *A61F 2002/061* (2013.01); *A61F 2/064* (2013.01); *A61F 2002/065* (2013.01); *A61F 2002/067* (2013.01); *A61F 2250/0039* (2013.01)

(56) References Cited

U.S. PATENT DOCUMENTS

| | | |
|---|---|---|
| 5,231,989 A | 8/1993 | Middleman et al. |
| 5,507,769 A * | 4/1996 | Marin .................... A61M 29/02 606/198 |
| 5,549,860 A * | 8/1996 | Charlesworth ......... A61L 27/56 264/154 |
| 5,562,724 A * | 10/1996 | Vorwerk .................... A61F 2/07 606/198 |
| 5,575,817 A | 11/1996 | Martin |
| 5,683,449 A | 11/1997 | Marcade |
| 5,695,517 A | 12/1997 | Marin et al. |
| 5,755,772 A | 5/1998 | Evans et al. |
| 5,843,160 A | 12/1998 | Rhodes |
| 5,855,598 A | 1/1999 | Pinchuk |
| 5,906,641 A * | 5/1999 | Thompson ............... A61F 2/856 606/191 |
| 5,928,181 A * | 7/1999 | Coleman .......... A61B 17/12136 604/8 |
| 5,984,955 A * | 11/1999 | Wisselink ............... A61F 2/954 623/1.35 |
| 6,059,824 A | 5/2000 | Taheri |
| 6,171,334 B1 | 1/2001 | Cox |
| 6,187,033 B1 * | 2/2001 | Schmitt ..................... A61F 2/06 623/1.35 |
| 6,210,429 B1 | 4/2001 | Vardi et al. |
| 6,280,464 B1 | 8/2001 | Hayashi |
| 6,306,141 B1 | 10/2001 | Jervis |
| 6,325,819 B1 * | 12/2001 | Pavcnik .................... A61F 2/07 606/198 |
| 6,325,826 B1 | 12/2001 | Vardi et al. |
| 6,344,056 B1 | 2/2002 | Dehdashtian |
| 6,395,018 B1 | 5/2002 | Castaneda |
| 6,428,565 B1 | 8/2002 | Wisselink |
| 6,585,756 B1 | 7/2003 | Strecker |
| 6,592,615 B1 | 7/2003 | Marcade et al. |
| 6,595,963 B1 * | 7/2003 | Barbut ................ A61M 1/3653 604/9 |
| 6,645,242 B1 | 11/2003 | Quinn |
| 6,676,699 B2 | 1/2004 | Shiu |
| 6,878,164 B2 * | 4/2005 | Kujawski .................. A61F 2/07 623/1.36 |
| 7,144,421 B2 | 12/2006 | Carpenter et al. |
| 7,294,147 B2 | 11/2007 | Hartley |
| 7,407,509 B2 * | 8/2008 | Greenberg ................ A61F 2/07 623/1.35 |
| 7,435,253 B1 | 10/2008 | Hartley et al. |
| 7,537,606 B2 | 5/2009 | Hartley et al. |
| 7,550,004 B2 | 6/2009 | Bahler et al. |
| 7,641,646 B2 | 1/2010 | Kennedy, II |
| 7,663,310 B2 * | 2/2010 | Lee .................... H10K 59/1201 313/506 |
| 7,731,744 B1 | 6/2010 | Cox |
| 7,763,063 B2 | 7/2010 | Arbefeuille et al. |
| 7,828,837 B2 * | 11/2010 | Khoury .................... A61F 2/07 623/1.35 |
| 7,854,758 B2 | 12/2010 | Taheri |
| 8,007,605 B2 | 8/2011 | Arbefeuille et al. |
| 8,021,419 B2 * | 9/2011 | Hartley .................... A61F 2/07 623/1.13 |
| 8,052,736 B2 | 11/2011 | Doig et al. |
| 8,062,349 B2 | 11/2011 | Moore et al. |
| 8,070,790 B2 | 12/2011 | Berra et al. |
| 8,105,372 B1 | 1/2012 | Chuter |
| 8,167,930 B2 | 5/2012 | Allen et al. |
| 8,172,895 B2 | 5/2012 | Anderson et al. |
| 8,267,988 B2 | 9/2012 | Hamer et al. |
| 8,273,115 B2 | 9/2012 | Hamer et al. |
| 8,292,943 B2 | 10/2012 | Berra et al. |
| 8,308,790 B2 | 11/2012 | Arbefeuille et al. |
| 8,333,800 B2 | 12/2012 | Bruszewski et al. |
| 8,337,546 B2 | 12/2012 | Bruszewski |
| 8,361,134 B2 | 1/2013 | Hartley et al. |
| 8,394,136 B2 | 3/2013 | Hartley et al. |
| 8,474,120 B2 | 7/2013 | Hagaman et al. |
| 8,500,792 B2 | 8/2013 | Berra |
| 8,523,934 B2 | 9/2013 | Purdy |
| 8,545,549 B2 * | 10/2013 | Hartley .................... A61F 2/07 623/1.13 |
| 8,574,284 B2 | 11/2013 | Roeder et al. |
| 8,574,288 B2 | 11/2013 | Hartley et al. |
| 8,636,788 B2 | 1/2014 | Arbefeuille et al. |
| 8,663,310 B2 | 3/2014 | Greenberg et al. |
| 8,672,993 B2 | 3/2014 | Chuter et al. |
| 8,740,963 B2 | 6/2014 | Arbefeuille et al. |
| 8,753,386 B2 | 6/2014 | Shaw |
| 8,771,336 B2 * | 7/2014 | Roeder .................... A61F 2/07 623/1.13 |
| 8,795,349 B2 | 8/2014 | Huser et al. |
| 8,870,939 B2 | 10/2014 | Roeder et al. |
| 8,870,946 B1 | 10/2014 | Quinn |
| 8,940,040 B2 | 1/2015 | Shahriari |
| 8,945,202 B2 | 2/2015 | Mayberry et al. |
| 8,945,203 B2 * | 2/2015 | Shalev .................... A61F 2/90 623/1.13 |
| 8,945,205 B2 | 2/2015 | Greenberg |
| 8,992,593 B2 | 3/2015 | Chuter et al. |
| 8,998,970 B2 | 4/2015 | Arbefeuille et al. |
| 8,998,971 B1 * | 4/2015 | Kelly ........................ A61F 2/07 623/1.11 |
| 9,034,027 B2 | 5/2015 | Ivancev |
| 9,095,456 B2 | 8/2015 | Ivancev et al. |
| 9,101,506 B2 | 8/2015 | Arbefeuille et al. |
| 9,149,382 B2 | 10/2015 | Greenberg et al. |
| 9,173,755 B2 | 11/2015 | Berra et al. |
| 9,198,786 B2 | 12/2015 | Moore et al. |
| 9,220,617 B2 | 12/2015 | Berra |
| 9,233,015 B2 | 1/2016 | Geusen et al. |
| 9,259,336 B2 | 2/2016 | Schaeffer et al. |
| 9,320,631 B2 | 4/2016 | Moore et al. |
| 9,333,104 B2 | 5/2016 | Ouellette et al. |
| 9,345,595 B2 | 5/2016 | Brocker et al. |
| 9,364,314 B2 | 6/2016 | Berra et al. |
| 9,408,734 B2 | 8/2016 | Arbefeuille et al. |
| 9,408,735 B2 | 8/2016 | Arbefeuille et al. |
| 9,439,751 B2 | 9/2016 | White et al. |
| 9,463,102 B2 | 10/2016 | Kelly |
| 9,554,929 B2 | 1/2017 | Arbefeuille et al. |
| 9,561,124 B2 | 2/2017 | Arbefeuille et al. |
| 9,592,112 B2 | 3/2017 | Arbefeuille et al. |
| 9,597,209 B2 | 3/2017 | Khoury |
| 9,649,188 B2 | 5/2017 | Hartley |
| 9,655,711 B2 * | 5/2017 | Hartley .................... A61F 2/856 |
| 9,655,712 B2 | 5/2017 | Berra et al. |
| 9,724,187 B2 | 8/2017 | Ivancev et al. |
| 9,827,123 B2 | 11/2017 | Arbefeuille et al. |
| 9,855,130 B2 | 1/2018 | Roeder et al. |
| 9,861,505 B2 | 1/2018 | Khoury |
| 9,877,857 B2 | 1/2018 | Arbefeuille et al. |
| 9,907,686 B2 | 3/2018 | Ouellette et al. |
| 9,913,743 B2 | 3/2018 | Arbefeuille et al. |
| 9,925,080 B2 | 3/2018 | Arbefeuille et al. |
| 9,993,325 B2 * | 6/2018 | Ren ........................ A61F 2/958 |
| 10,105,248 B2 | 10/2018 | Berra et al. |
| 10,105,250 B2 | 10/2018 | Berra |

(56) References Cited

U.S. PATENT DOCUMENTS

| | | | |
|---|---|---|---|
| 10,182,930 B2 | 1/2019 | Moore et al. | |
| 10,213,291 B2 | 2/2019 | Berra et al. | |
| 10,299,951 B2 | 5/2019 | Arbefeuille et al. | |
| 10,307,275 B2 | 6/2019 | Berra et al. | |
| 10,390,929 B2 | 8/2019 | Arbefeuille et al. | |
| 10,390,930 B2* | 8/2019 | Arbefeuille | A61F 2/07 |
| 10,390,932 B2* | 8/2019 | Lostetter | A61F 2/07 |
| 10,524,893 B2* | 1/2020 | Parodi | A61F 2/848 |
| 10,631,972 B2* | 4/2020 | Greenberg | A61F 2/856 |
| 10,646,365 B2 | 5/2020 | Berra et al. | |
| 10,898,357 B2 | 1/2021 | Arbefeuille et al. | |
| 10,918,509 B2 | 2/2021 | Moore et al. | |
| 11,065,100 B2 | 7/2021 | Parodi et al. | |
| 11,154,392 B2 | 10/2021 | Lostetter | |
| 11,395,750 B2* | 7/2022 | Lostetter | A61F 2/89 |
| 11,446,167 B2* | 9/2022 | Parodi | A61F 2/856 |
| 11,547,549 B2* | 1/2023 | Arbefeuille | A61F 2/966 |
| 11,638,639 B2* | 5/2023 | Dake | A61F 2/07 623/1.11 |
| 11,918,451 B2 | 3/2024 | Parodi et al. | |
| 2002/0013620 A1 | 1/2002 | Kujawski | |
| 2002/0052643 A1 | 5/2002 | Wholey et al. | |
| 2002/0062133 A1 | 5/2002 | Gilson et al. | |
| 2002/0156521 A1* | 10/2002 | Ryan | A61F 2/90 623/1.13 |
| 2003/0109919 A1* | 6/2003 | Gantt | A61F 2/06 623/901 |
| 2003/0120333 A1* | 6/2003 | Ouriel | A61F 2/07 623/1.14 |
| 2003/0130725 A1 | 7/2003 | DePalma et al. | |
| 2003/0157805 A1 | 8/2003 | Schultz et al. | |
| 2003/0199967 A1 | 10/2003 | Hartley et al. | |
| 2003/0204242 A1 | 10/2003 | Zarins et al. | |
| 2005/0059923 A1 | 3/2005 | Gamboa | |
| 2005/0131518 A1 | 6/2005 | Hartley et al. | |
| 2005/0131523 A1 | 6/2005 | Bashiri et al. | |
| 2005/0177222 A1 | 8/2005 | Mead | |
| 2006/0095118 A1 | 5/2006 | Hartley | |
| 2006/0184228 A1 | 8/2006 | Khoury | |
| 2006/0229707 A1 | 10/2006 | Khoury | |
| 2007/0055350 A1 | 3/2007 | Erickson et al. | |
| 2007/0106368 A1 | 5/2007 | Vonderwalde | |
| 2007/0142896 A1 | 6/2007 | Anderson et al. | |
| 2007/0168013 A1 | 7/2007 | Douglas | |
| 2007/0198078 A1 | 8/2007 | Berra et al. | |
| 2007/0203566 A1 | 8/2007 | Arbefeuille et al. | |
| 2008/0091260 A1 | 4/2008 | Pomeranz et al. | |
| 2008/0109066 A1 | 5/2008 | Quinn | |
| 2008/0114444 A1 | 5/2008 | Yu | |
| 2008/0183273 A1 | 7/2008 | Mesana et al. | |
| 2008/0264102 A1 | 10/2008 | Berra | |
| 2009/0048663 A1* | 2/2009 | Greenberg | A61F 2/07 623/1.35 |
| 2009/0125100 A1 | 5/2009 | Mead | |
| 2009/0264988 A1 | 10/2009 | Mafi et al. | |
| 2009/0319022 A1 | 12/2009 | Hartley et al. | |
| 2010/0057186 A1 | 3/2010 | West et al. | |
| 2011/0087318 A1 | 4/2011 | Daugherty et al. | |
| 2011/0118821 A1 | 5/2011 | Brocker et al. | |
| 2011/0208288 A1 | 8/2011 | Arbefeuille et al. | |
| 2011/0245906 A1 | 10/2011 | DiMatteo et al. | |
| 2011/0257731 A1 | 10/2011 | Hartley et al. | |
| 2011/0270380 A1 | 11/2011 | Bruszewski | |
| 2011/0313503 A1 | 12/2011 | Berra et al. | |
| 2012/0046728 A1 | 2/2012 | Huser et al. | |
| 2012/0089220 A1 | 4/2012 | Lualdi | |
| 2012/0123464 A1 | 5/2012 | Rasmussen et al. | |
| 2012/0130472 A1 | 5/2012 | Shaw | |
| 2012/0245672 A1 | 9/2012 | Arbefeuille et al. | |
| 2012/0271401 A1 | 10/2012 | Bruszewski et al. | |
| 2012/0296414 A1 | 11/2012 | Hartley | |
| 2012/0310324 A1 | 12/2012 | Benary et al. | |
| 2013/0013053 A1 | 1/2013 | Hartley et al. | |
| 2013/0079870 A1 | 3/2013 | Roeder et al. | |
| 2013/0138199 A1 | 5/2013 | Ivancev et al. | |
| 2013/0197627 A1 | 8/2013 | Jensen et al. | |
| 2013/0211506 A1* | 8/2013 | Dake | A61F 2/954 623/1.35 |
| 2013/0282103 A1 | 10/2013 | Madjarov et al. | |
| 2014/0046428 A1 | 2/2014 | Cragg et al. | |
| 2014/0135890 A9 | 5/2014 | Berra | |
| 2014/0243949 A1 | 8/2014 | Shaw | |
| 2014/0243952 A1 | 8/2014 | Parodi | |
| 2014/0277347 A1 | 9/2014 | Daugherty et al. | |
| 2014/0277379 A1 | 9/2014 | Vogel et al. | |
| 2015/0202066 A1 | 7/2015 | Berra et al. | |
| 2016/0184077 A1 | 6/2016 | Choubey et al. | |
| 2016/0184078 A1 | 6/2016 | Choubey et al. | |
| 2016/0184115 A1 | 6/2016 | Ondersma et al. | |
| 2017/0007392 A1 | 1/2017 | Louren et al. | |
| 2017/0281382 A1 | 10/2017 | Lostetter et al. | |
| 2017/0319359 A1 | 11/2017 | Mehta | |
| 2017/0325977 A1 | 11/2017 | Sarac et al. | |
| 2017/0340462 A1 | 11/2017 | Lostetter | |
| 2018/0078394 A1 | 3/2018 | Zimmerman et al. | |
| 2018/0140448 A1 | 5/2018 | Arbefeuille et al. | |
| 2018/0206972 A1 | 7/2018 | Arbefeuille et al. | |
| 2019/0328557 A1 | 10/2019 | Lostetter | |
| 2020/0085560 A1 | 3/2020 | Parodi et al. | |
| 2021/0307895 A1 | 10/2021 | Parodi et al. | |
| 2022/0008191 A1 | 1/2022 | Lostetter | |
| 2022/0313459 A1 | 10/2022 | Lostetter | |

FOREIGN PATENT DOCUMENTS

| | | | |
|---|---|---|---|
| CN | 102379757 A | | 3/2012 |
| CN | 102488575 A | | 6/2012 |
| CN | 102641164 A | | 8/2012 |
| CN | 102973303 A | * | 3/2013 |
| CN | 103209659 A | | 7/2013 |
| CN | 103876860 A | | 6/2014 |
| CN | 104066401 A | | 9/2014 |
| CN | 203841852 U | | 9/2014 |
| CN | 104287871 A | | 1/2015 |
| CN | 102973303 B | | 2/2015 |
| CN | 104367400 A | | 2/2015 |
| CN | 104546221 A | | 4/2015 |
| CN | 105030373 A | | 11/2015 |
| EP | 0786972 B1 | | 1/2004 |
| EP | 1487380 B1 | | 2/2008 |
| EP | 2450006 B1 | | 1/2015 |
| JP | 2010/535580 A | | 11/2010 |
| JP | 2015519178 A | | 7/2015 |
| WO | WO-2001/032103 A1 | | 5/2001 |
| WO | WO-2002/038085 A1 | | 5/2002 |
| WO | WO-2005/023149 A2 | | 3/2005 |
| WO | WO-2006/034276 A1 | | 3/2006 |
| WO | WO-2006/113501 A1 | | 10/2006 |
| WO | WO-2007/092276 A2 | | 8/2007 |
| WO | WO-2007/123956 A2 | | 11/2007 |
| WO | WO-2008021557 A1 | * | 2/2008 ............... A61F 2/07 |
| WO | WO-2010/005524 A2 | | 1/2010 |
| WO | WO-2010/024879 A1 | | 3/2010 |
| WO | WO-2011/056638 A1 | | 5/2011 |
| WO | WO-2013/071222 A1 | | 5/2013 |
| WO | WO-2013/074990 A1 | | 5/2013 |
| WO | WO-2014/149022 A1 | | 9/2014 |
| WO | WO-2015/188775 A1 | | 12/2015 |
| WO | WO-2017/218474 A1 | | 12/2017 |
| WO | WO-2018/026768 A1 | | 2/2018 |
| WO | WO-2018/031632 A1 | | 2/2018 |

OTHER PUBLICATIONS

Non-Final Office Action for U.S. Appl. No. 15/604,032 dated Feb. 11, 2019.

Notice of Allowance for U.S. Appl. No. 13/788,724, dated Nov. 28, 2016.

Notice of Allowance for U.S. Appl. No. 15/417,467, dated May 22, 2019.

U.S. Office Action for U.S. Appl. No. 13/788,724 dated Apr. 21, 2016.

(56) References Cited

OTHER PUBLICATIONS

U.S. Office Action for U.S. Appl. No. 13/788,724 dated Apr. 25, 2015.
U.S. Office Action for U.S. Appl. No. 14/272,818 dated Feb. 1, 2017.
U.S. Office Action for U.S. Appl. No. 14/272,818 dated Mar. 17, 2016.
U.S. Office Action for U.S. Appl. No. 14/272,818 dated May 8, 2018.
U.S. Office Action for U.S. Appl. No. 14/272,818 dated Sep. 9, 2015.
U.S. Office Action for U.S. Appl. No. 14/272,818 dated Aug. 25, 2016.
U.S. Office Action for U.S. Appl. No. 14/861,479 dated May 1, 2017.
U.S. Office Action for U.S. Appl. No. 15/417,467 dated Nov. 30, 2018.
U.S. Office Action for U.S. Appl. No. 13/788,724 dated Apr. 28, 2015.
Browne et al., "Endovascular and surgical techniques: A fenestrated covered suprarenal aortic stent," Eur J Vasc Endovasc Surg, 18:445-449 (1999).
Chuter et al., "Development of a branched stent-graft for endovascular repair of aortic arch aneurysms," J Endovasc Ther, 10:940-945 (2003).
Chuter et al., "Modular branched stent graft for endovascular repair of aortic arch aneurysm and dissection," J Vasc Surg, 38:859-863 (2003).
European Search Report for EP Application No. 16189498 dated Jan. 18, 2017.
Extended European Search Report for EP Application No. 19156496.2 dated Jul. 15, 2019.
Funovics, "Branched endografts for aortic arch aneurysms—How close are we?," CIRSE 2011 Conference, Munich Germany, Session No. 802.3 (Sep. 10-14, 2011).
Funovics, "TEVAR in the ascending aorta: A new frontier for endografting—preliminary results and technology transfer," Focus Meeting, Bolton Medical Inc., Barcelona, Spain (Oct. 2011).
Inoue et al., "Aortic arch reconstruction by transluminally placed endovascular branched stent graft," Circulation, 100(Suppl II):II-316-11-321 (1999).
Inoue et al., "Clinical endovascular placement of branched graft for type B aortic dissection," J Thorac Cardiovasc Surg, 112:1111-1113 (1996).
Inoue et al., "Transluminal endovascular branched graft placement for a pseudoaneurysm: Reconstruction of the descending thoracic aorta including the celiac axis," J Thorac Cardiovasc Surg, 114:859-861 (1997).
International Preliminary Report on Patentability for International Application No. PCT/US2012/064612 dated May 22, 2014.
International Preliminary Report on Patentability for International Application No. PCT/US2012/065622 dated May 20, 2014.
International Preliminary Report on Patentability for International Application No. PCT/US2015/051470 dated Mar. 28, 2017.
International Preliminary Report on Patentability for International Application No. PCT/US2017/034223 dated Nov. 27, 2018.
International Preliminary Report on Patentability for International Application No. PCT/US2017/046062 dated Feb. 12, 2019.
International Preliminary Report on Patentability for International Application No. US/2012/064612 dated May 13, 2014.
International Search Report and Written Opinion for International Application No. PCT/US2017/025912 dated Jun. 26, 2017.
International Search Report and Written Opinion for International Application No. PCT/US12/64612 dated Apr. 2, 2013.
International Search Report and Written Opinion for International Application No. PCT/US2012/065622 dated Mar. 1, 2013.
International Search Report and Written Opinion for International Application No. PCT/US2015/051470 dated Dec. 4, 2015.
International Search Report and Written Opinion for International Application No. PCT/US2017/034223 dated Aug. 22, 2017.
International Search Report and Written Opinion for International Application No. PCT/US2017/046062 dated Oct. 24, 2017.
Kinney et al., "Repair of mycotic paravisceral aneurysm with a fenestrated stent-graft," J Endovasc Ther, 7:192-197 (2000).
Lioupis et al., "Treatment of aortic arch aneurysms with a modular transfemoral multibranched stent graft: Initial experience," European Journal of Vascular and Endovascular Surgery, 43:525-532 (2012).
Martinelli, "Partial ascending aorta and total arch reconstruction with bolton medical branched thoracic endograft," Cardiovascular Surgery Meeting, Bologna, Italy (Nov. 14-15, 2011).
Oderich et al., "Initial experience with the Gore Excluder thoracoabdominal branch endoprosthesis," Supplement to Endovascular Today, 15(3):12-16 (2016).
Ouriel et al., "Branched device to preserve hypogastric arterial flow with thoracoabdominal aneurysm repair," J Vasc Surg, 37:481 (2003).
Simring et al., "Total endovascular repair of the arch: Branched endografting makes it easy," Tecnicas Endovasculares, 14(1):3712-3716 (2011).
Wisselink et al., "Endoluminal Repair of Aneurysms Containing Ostia of Essential Branch Arteries: An Experimental Model," J Endovasc Surg, 6:171-179 (1999).

* cited by examiner

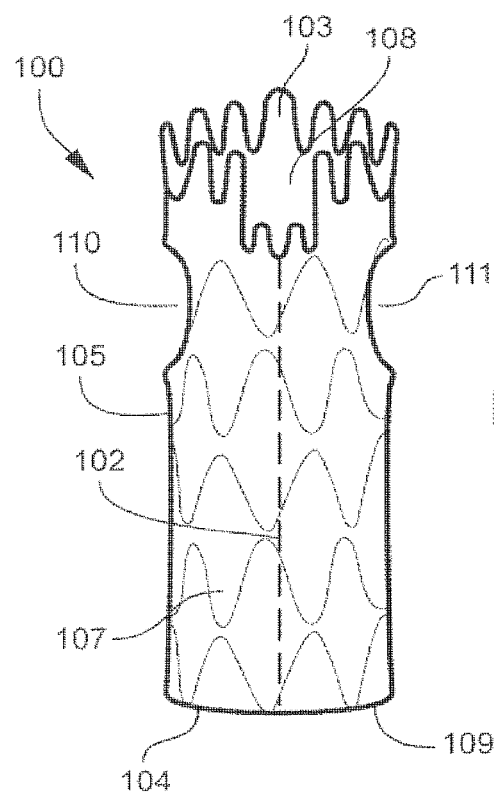 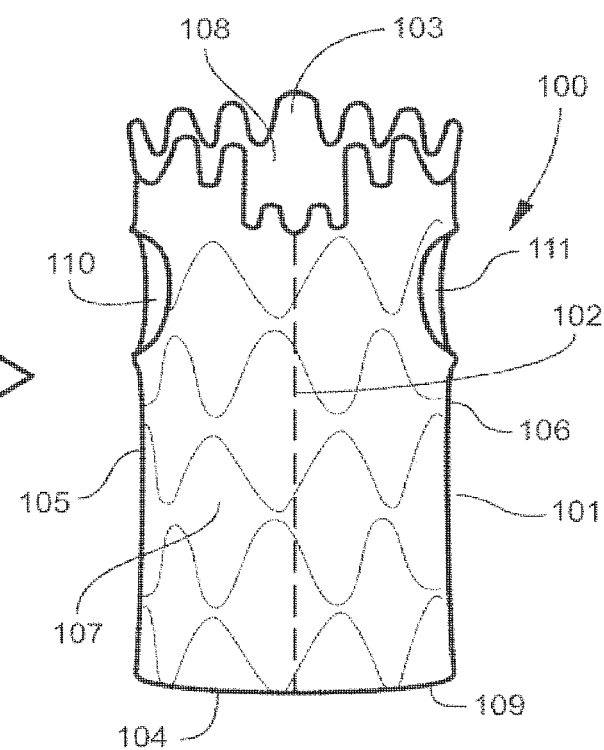
Fig. 1A　　　　　　Fig. 1B
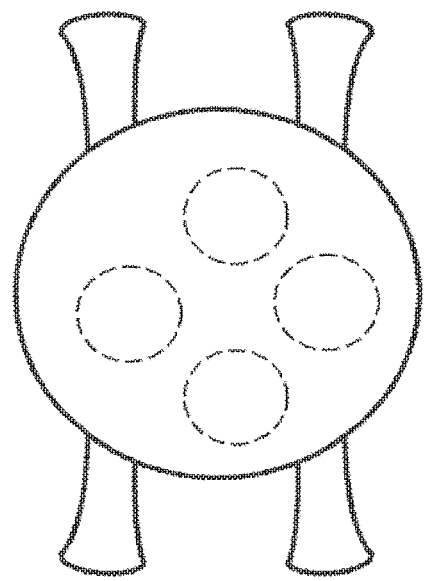
Fig. 1C

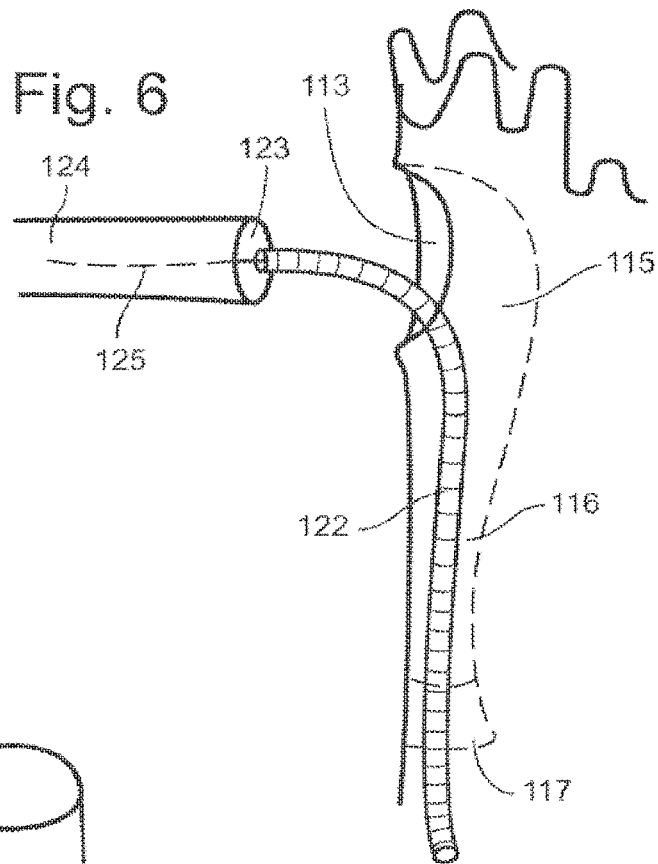
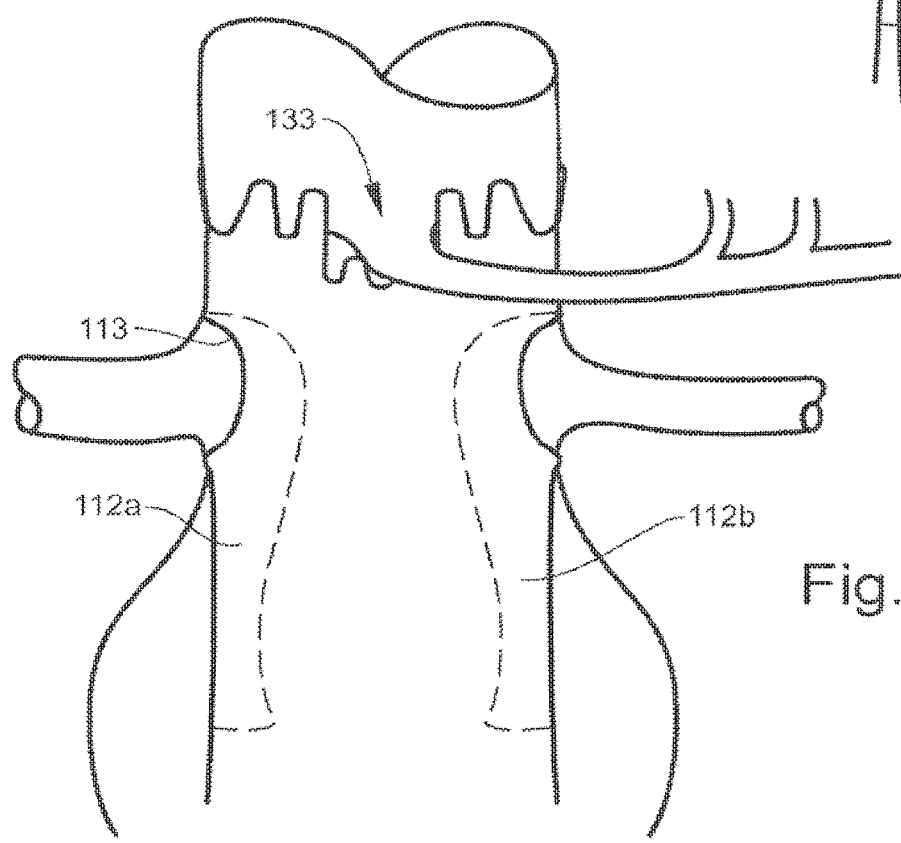

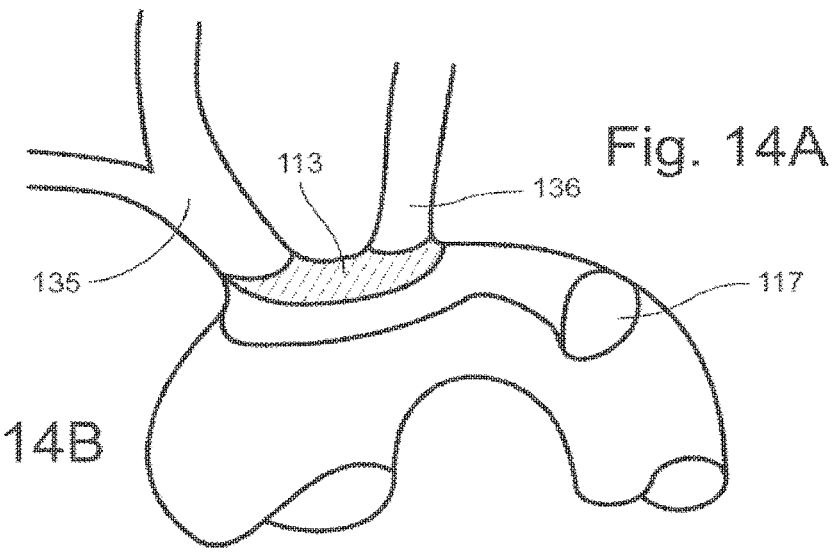
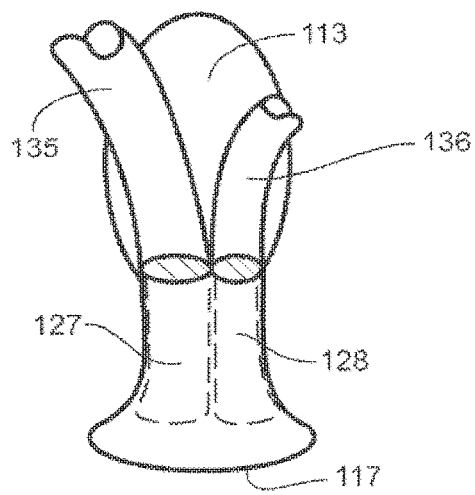
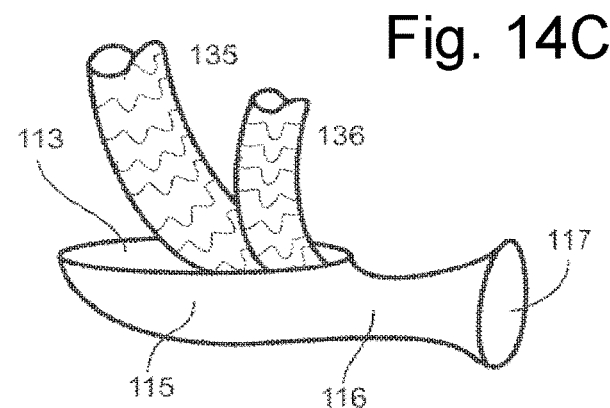
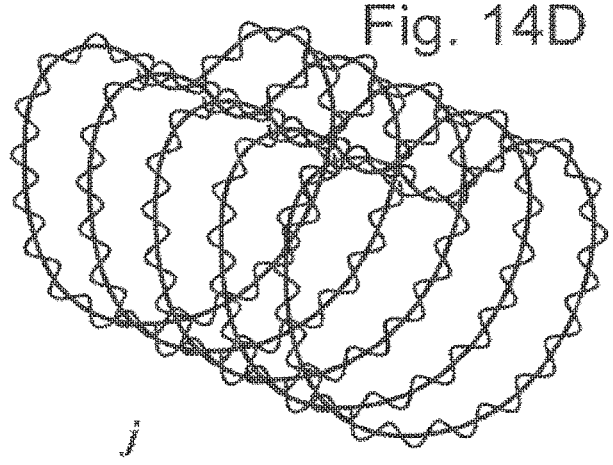
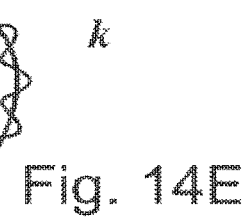
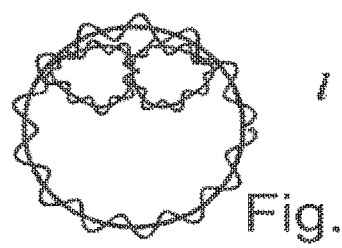

UNIVERSAL ENDOVASCULAR GRAFTS

RELATED APPLICATIONS

This application is a continuation of U.S. application Ser. No. 14/272,818, filed May 8, 2014, which is a continuation of International Application No. PCT/US2012/064612, filed on Nov. 12, 2012, which claims priority to U.S. Provisional Application No. 61/559,016 filed Nov. 11, 2011 and U.S. Provisional Application No. 61/559,021 also filed on Nov. 11, 2011. The disclosures of U.S. Provisional Patent Application 61/559,016 and U.S. Provisional Application No. 61/559,021 are incorporated by reference herein in their entirety.

FIELD OF THE INVENTION

The present invention relates generally to endovascular grafts ("endografts") for evaluation and repair of damaged or aneurismal blood vessels. More particularly, it relates to universal fenestrated and universal branched endografts for repair of blood vessels with branches, methods for repairing blood vessels and for making connection with one or more branches.

BACKGROUND OF THE INVENTION

Endografts are artificial grafts typically composed of metal and fabric that are placed inside the arteries or veins to treat aneurysms, dissections, stenosis or injuries. Endografts cover the diseased segments of the vessels, and typically the ends of endografts are positions against non-diseased portions. Placement of endografts typically is done from a remote site, usually the common femoral artery.

Since the first English publication of a study describing the clinical application of an endograft to treat an aneurysm (Annals of Vascular Surgery 1991; 5:491), endografting has expanded worldwide. In 2010, approximately 107,000 endografts were applied for aortic aneurysms globally.

In many cases, the damaged or defected portion of the vessel being treated may include branches. For example, in the case of the abdominal aorta, there are at least three branch vessels, including the celiac, mesenteric, and renal arteries, leading to various other organs. Thus, when the damaged portion of the vessel includes one or more of these branch vessels, some accommodation must be made to ensure that the endograft does not block or hinder blood flow through the branch vessel.

Attempts to maintain blood flow to branch vessels have included providing one or more fenestrations or holes in the side wall of the endograft. Other attempts have included providing an endograft in which the branch vessel portion of the vessel is spanned by wires or the like. Generally, this treatment involves aligning the fenestrations with the branch vessels, which may extend approximately at right angles on both sides from the aorta.

In many cases, the vasculature is not symmetric. In addition, even with symmetrical vasculature, physiological forces may cause a previously placed branch vessel endograft to shift causing the position of the fenestration to offset from the branch. In other instances, the diseased vasculature may extend into the branch vessel itself.

When treating a vessel with an endograft, it is sometimes beneficial to deploy a secondary endograft extending from the primary endograft to a side branch vessel so that the blood flow into the branch vessel is not impeded. Branch vessel endografts can form a connection to primary endografts through fenestrations to complete the prosthesis. Furthermore, some aneurysms extend into the branch vessels in both the thoracic and abdominal aorta. Deploying prostheses with prosthetic branches into these vessels may help prevent expansion and/or rupture of these aneurysms.

Limitations for the use of endografts in the aorta are related to short or angulated landing zones. When visceral or supra-aortic branches split off from an aneurysm, endografts need to have fenestrations or branches similar to those used in short proximal necks (landing zones). When fenestrations or branches are needed, custom-made devices are constructed that take into account distances and angles indicated in aortic images of a patient. Custom made devices have been constructed until now with good results, but such devices are expensive and take a relatively long time to manufacture. Further, the custom nature of the device adds complexity to the procedure of implantation, due to, among other reasons, inconsistent designs. Additionally, it is frequently difficult to accurately and precisely guide the instrumentation needed to cannulate the branch to the branch ostium. Thus, it would be beneficial for an endograft to have structures connecting the lumen of the endograft to the fenestration and the branch artery ostium; thus facilitating cannulation of the branch arteries and a continuation of procedures without extra incisions or unnecessary arterial approaches. Accordingly, there is need to address these issues.

BRIEF SUMMARY OF THE INVENTION

In order to facilitate the procedure and provide an "off the shelf" device, the following invention was developed. The universal endografts described below could be used for all, or most, of the patients with similar conditions.

Referring now to the universal fenestrated endograft of the present invention, one aspect of the invention relates to an endograft with orifices or fenestrations to facilitate connection between an endograft placed in an artery or vessel and branches of other arteries and vessels. In one embodiment, fenestrations are located within the walls of an endograft. In another embodiment, the endograft may additional comprise cannulation members engaged to said fenestrations. Cannulation members generally comprise an external orifice, a cavity, a tubular segment, and an internal orifice. The external orifice may further comprise an inner and outer rim. In one embodiment, the internal orifice of the cannulation member from the lumen of the universal fenestrated endograft. This direct connection from the lumen of the universal fenestrated endograft to the branch artery facilitates efficient treatment of branch arteries without the need of extra incision or arterial approaches other than femoral access.

As the external orifice of the universal fenestrated endograft of the present invention has dimensions that accommodate most arterial or venous branch morphology, the device is called a universal fenestrated endograft. For example, in one embodiment, the external orifice of the cannulation member may be wide enough to accommodate anatomical variations of the aortic arch, as well as areas of the visceral arteries in the abdominal aorta.

In one embodiment of the universal fenestrated endograft of the present invention, openings or fenestrations may cover all of the variations of the site of the extensions of the branches of the vessels. The tubular segment of the cannulation member may connect to the proximal lumen of the branch vessel through an endograft interposed between them. Furthermore, the inner orifice of the cannulation member may have a flared end to facilitate cannulation.

In another embodiment of the universal fenestrated endograft of the present invention, fenestrations and the corresponding cannulation member may be constructed as a part of the main universal fenestrated endograft wherein the cannulation member is independent or shares segments between the cannulation member and the endograft.

Catheters and other instrumentation may be introduced in the tubular segment of the cannulation member reaching the cavity of the cannulation member and the fenestration. Ostia of the branch vessels may be cannulated and connection with a tubular endograft is established between the tubular segment of the cannulation member and the trunk of the branch vessel, for example, the initial about 1.5 to 2 cm of the vessel.

In another aspect of the universal fenestrated endograft of the present invention, when the cannulation member accommodates multiple branches, in one embodiment, procedures may be performed from different chambers constructed within the tubular segment of the cannulation member to the different vessel branches. In another embodiment, independent cannulation members may be constructed wherein each cannulation member uses the same universal fenestration to access the different vessel branches.

In another aspect of the universal fenestrated endograft of the present invention, walls of the cannulation member may be a part of the endograft, constitute a braided cannulation member attached to the edge of the fenestration, or make up a malleable cannulation member attached to the edge of the fenestration, wherein, in this latter case, a balloon of very low profile is placed inside the cannulation member and the cannulation member is compressed and collapsed over the balloon.

In another aspect of the universal fenestrated endograft of the present invention, guiding elements, for example, guide wires or fabric threads, are used to guide catheters inside the cannulation member. Wires and threads may be attached outside the fenestration, pass the fenestration and come out through an orifice of the valve of the introducer sheath.

In another aspect of the universal fenestrated endograft of the present invention, segments of the aorta or iliac arteries in which universal fenestrated endograft could be used include: an aortic arch; visceral segment of the abdominal aorta; and iliac bifurcation in cases of iliac aneurysms.

Another embodiment of the invention relates to a universal fenestrated endograft having a body extended along a longitudinal axis, the body being expandable and having a first end, a second end, a first wall, a second wall, and an interior passage or lumen there between when expanded. The body may include openings in communication with the passage at the first and second ends, the openings being substantially transverse to the longitudinal axis. The body may include one or more lateral fenestrations in communication with the lumen at the first or second end. The body may have a necked portion between the ends and may further have a cannulation member contained therein.

In one embodiment, the body, including the cannulation member, has a braided construction.

In another embodiment, the body may comprise a scallop for receiving a branch artery, for example, the superior mesenteric artery. For example, a scallop may be used to prevent coverage of the superior mesenteric artery when a universal fenestrated endograft is used to connect the renal arteries.

Another embodiment of the invention relates to a method for repairing a patient's blood vessel. In the method a universal fenestrated endograft is obtained, as described herein and implanted to affect a therapeutic result.

Referring now to the universal branched endograft of the present invention, in one embodiment of the invention a universal branched endograft device comprises a tubular body with a main lumen and four branch lumens, with a large branch extending from the body. The large branch may be in fluid communication with the main lumen. The four branch lumens may be positioned about a circumference of the tubular body, and each configured to connect to a tubular endograft.

In one aspect of the first embodiment of the universal branched endograft, each branch lumen can include a tubular extension configured for connecting to a target branch artery.

In another aspect of the embodiment of the universal branched endograft, the large branch can be configured to connect with a distal aorta or an iliac artery.

In another aspect of the embodiment of the universal branched endograft, each lumen includes a stent-like frame.

In another aspect of the embodiment of the universal branched endograft, the tubular body is at least about 6 cm in length.

Another embodiment of the invention regards a method for using the universal branched device. In the method, the universal branched device may be obtained and implanted within a patient to treat a thoraco-abdominal aneurysm.

In one aspect of the method, a guiding element is fed from a femoral cut down to the thoracic aorta. The universal branched endograft with aortic extensions can be put into place via the guiding element, and the universal branched endograft is cannulated to a superior mesenteric artery (SMA), celiac axis and renal arteries.

BRIEF DESCRIPTION OF THE DRAWINGS

An embodiment[s] of the invention will now be described with reference to the accompanying drawings, in which:

FIG. 1A-C shows a universal fenestrated endograft (constricted and expanded) with two lateral universal fenestrations and a scallop at the first end of the endograft to prevent coverage of a branch artery. FIG. 1C shows an exterior view of a lateral fenestration covering four branch vessel positions.

FIG. 1B shows a braided cannulation member in an expanded and constricted state.

FIG. 6 shows a cannulation member, renal artery, and a catheter and guiding element cannulating the branch artery.

FIG. 7 shows an upper segment of the universal fenestrated endograft with two lateral cannulation members covering the renal arteries and a scallop for the superior mesenteric artery. Also shown is an aortic aneurysm.

FIG. 8A shows a cannulation member sharing walls with the main endograft. FIG. 8B shows a cannulation member that engages the wall at specific attachment points, for example the edge of the fenestration or external orifice.

FIGS. 14A-F show embodiments positioned within an aortic arch.

DETAILED DESCRIPTION OF THE INVENTION

Further scope of applicability of the present invention will become apparent from the detailed description given herein. However, it should be understood that the detailed description and examples provided herein, while indicating embodiments of the invention, are given by way of illustration only, since various changes and modifications within the spirit and scope of the invention will become apparent to those skilled in the art.

The present invention takes the form of an endovascular graft ("endograft") for use in the common catheter-based minimally-invasive surgical techniques, for example, in the examination and repair of the thoracic or abdominal aorta.

Figures 16A, 16B:
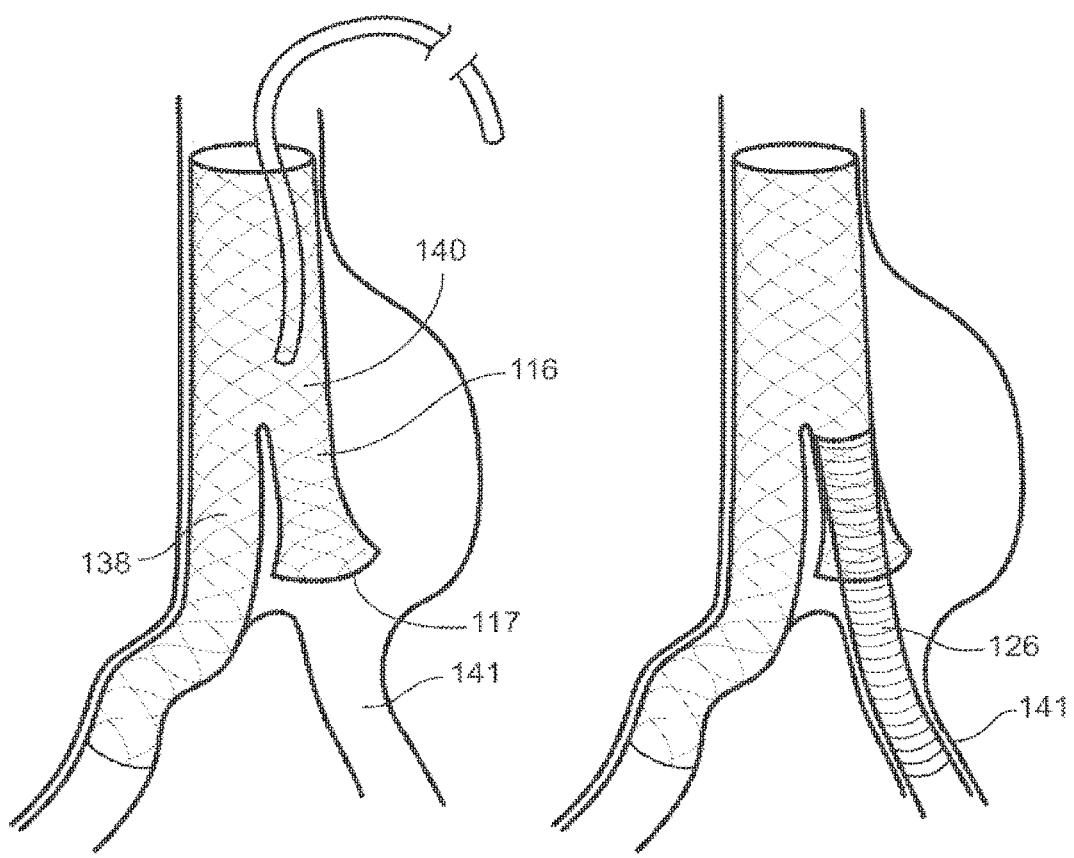
FIGS. 16A-B shows another application of the universal fenestrated endograft to common iliac artery aneurysms.

Referring now to the universal fenestrated endograft of the present invention, FIG. 1 shows an example of the universal fenestrated endograft 100 of the present invention. The universal fenestrated endograft 100 is generally tubular in shape with body 101 extended along a longitudinal axis 102, the body being expandable and having a first end 103, a second end 104, a first wall 105, a second wall 106, and an interior passage or lumen 107 there between. The body may include openings 108 and 109 in communication with the passage at the first and second ends respectively, the openings being substantially transverse to the longitudinal axis. The body may include one or more lateral fenestrations 110 and 111 in communication with the lumen. The body may have a necked portion between the ends and may furthermore have a cannulation member 112 contained therein as shown in FIG. 3. If desired, the universal fenestrated endograft 100 may also be made in a bifurcated configuration, similar to that shown in FIGS. 16A-B. The universal fenestrated endograft 100 may be made of polyester, polytetrafluoroethylene (PTFE) or any other suitable fabric. The universal fenestrated endograft 100 may be reinforced or unreinforced and stented or nonstented.

As discussed above, the universal fenestrated endograft 100 may have one or more fenestrations or openings (reference numbers 110 and 111 in FIG. 1) preferably assuming a substantially circular or oval shape largely depending on the branches to be treated. A fenestration may comprise of an orifice or opening in the wall of the universal fenestrated endograft. Because the external orifices of the fenestrated endograft of the present invention have dimensions that accommodate most arterial or venous branch morphology including variable distances, angles and profiles of one or more vessels, the device is called universal fenestrated endograft. For example, the renal arteries may branch from the aorta at the same level or at different levels. Similarly, some arteries extending from the aorta may be directed more anteriorly while others more posteriorly. The present invention is designed to accommodate such variants. For example, in one embodiment, said external orifice may be wide enough to accommodate anatomical variations of the aortic arch, as well as areas of the visceral arteries in the abdominal aorta. Diameter may of the opening may vary according to the area treated, for example, larger in the aortic arch and smaller in the juxta-renal area. In one embodiment, the universal fenestrations are between about 3 and about 7 cm in diameter depending on, for example, anatomical variations and the specific target branch vessel or vessels. In a preferred embodiment, the universal fenestrations are about 5 cm in diameter. In another preferred embodiment, the universal fenestrations are about 4 cm in diameter.

Figure 2:
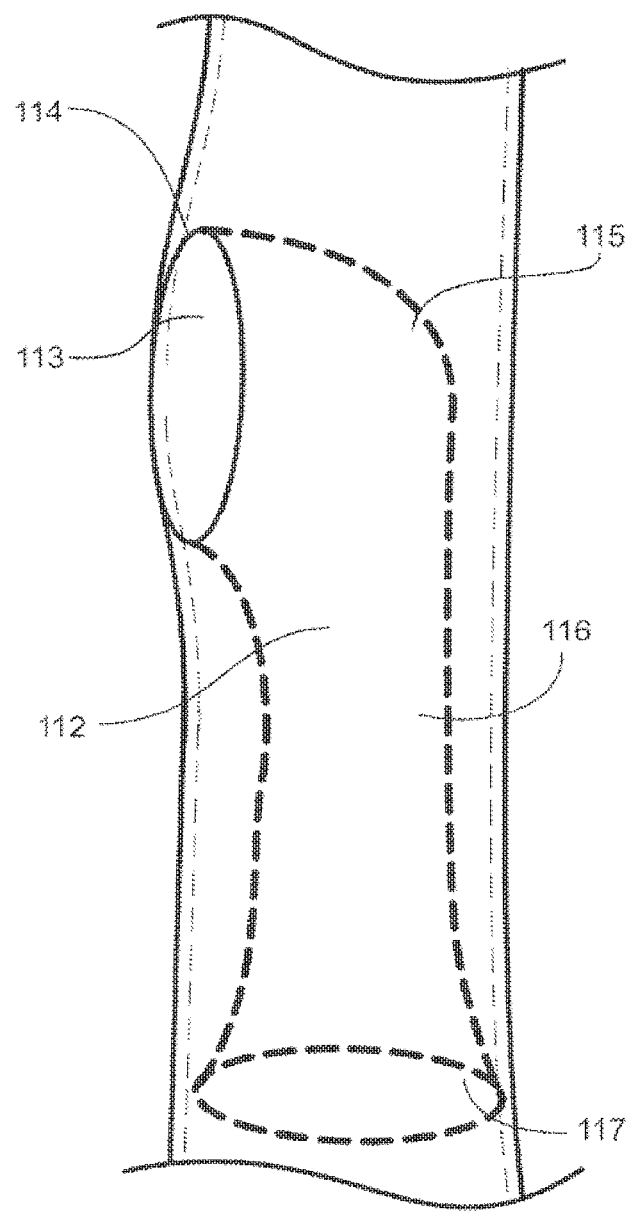
FIG. 2 shows an embodiment of a cannulation member and its components.
Figure 3A:
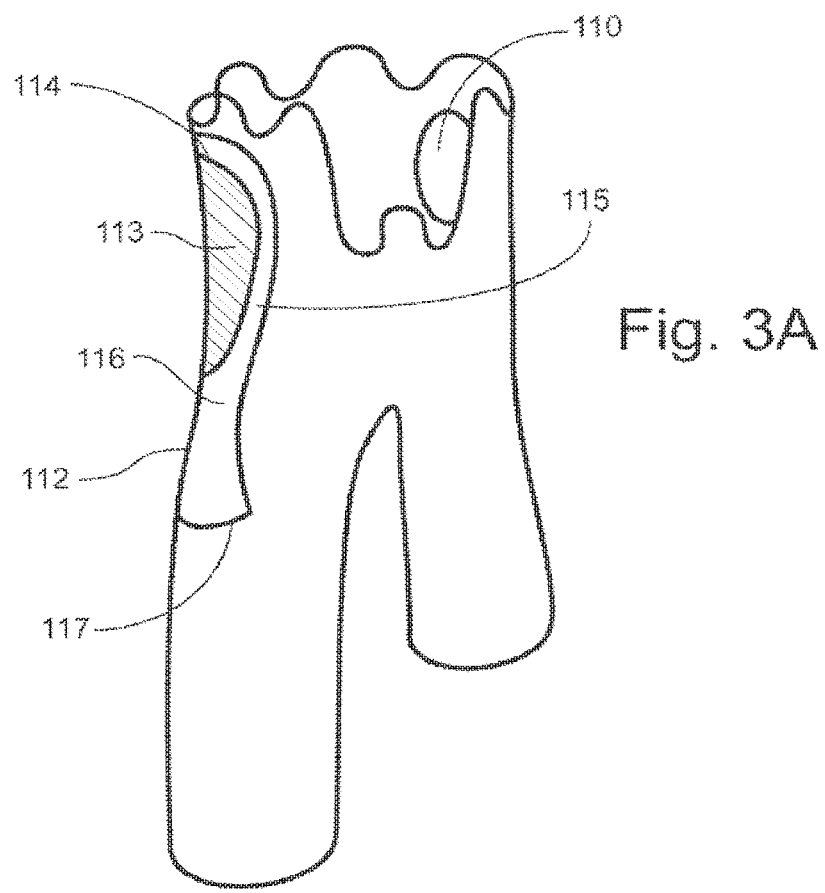
FIGS. 3A-B shows various embodiments, including a universal fenestrated endograft with two cannulation members engaged to a lateral universal fenestration.

Referring to FIG. 3A, in some embodiments of the present invention, fenestrations of the universal fenestrated endograft do not open directly into the lumen of the universal fenestrated endograft, rather they are engaged to one or more cannulation members 112 positioned inside the lumen of the universal fenestrated endograft. Referring now to FIG. 2, the cannulation member may comprise an external orifice 113, a rim 114, a cavity 115, a tubular segment 116, and an internal orifice 117. The external orifice 113 may be of the same or different dimension to the fenestration to which it is engaged. For example, in one embodiment, the external orifice is between about 3 and about 7 cm in diameter depending on, for example, anatomical variations and the specific target branch vessel or vessels. In a preferred embodiment, the external orifice is about 5 cm in diameter. In another preferred embodiment, the external orifice is about 4 cm in diameter. In some embodiments, the external orifice 113 may be substantially circular or substantially oval shaped. As an example, the external orifice 113 and fenestration may be circular and smaller in diameter for the renal, celiac and superior mesenteric artery targets (e.g. 3 cm) and more oval shaped and larger for the supra-aortic vessels (e.g., 7 cm).

The cannulation member may take any shape; however in some embodiments, the cannulation member is substantially funnel shaped, tubular shaped and/or cylindrical shaped depending on the components. For example, in some embodiments, tubular segment 116 is substantially tubular shaped. The orientation of the cannulation member 112 inside the universal fenestrated endograft may be vary depending on factors, such as for example, anatomical variations in the patient blood flow preservation needs, etc. For example, the longitudinal axis through the tubular segment of the cannulation member may be directed substantially parallel to (in either direction), oblique to, or at a 90° angle to the longitudinal axis of the body of the main universal fenestrated endograft. In some embodiments, cannulation members 112 may be either caudally and/or cranially directed.

For example, in procedures involving the aortic arch and carotid/innominate target branches, it may be beneficial to position external orifice 113 and cannulation member 112 in general such to prevent retrograde blood flow caused by extreme angles of approach. Thus, in the embodiment illustrated in FIG. 17A-B, the cannulation members 112a and 112b are obliquely angled to facilitate blood flow.

As described above, the cannulation member may be engaged to the side of the universal fenestrated endograft. As shown in FIG. 9, the cannulation member may share one of its an entire walls with the universal fenestrated endograft, may share part of one of its walls with the universal fenestrated endograft, or may have walls that are independent of the universal fenestrated endograft and engaged at one or more attachment point 118, 119, 120.

The tubular segment 116 of the cannulation member may be any dimension as long as it can accommodate the instrumentation necessary for the procedure being performed, for example catheters and/or guiding elements. For example, in some embodiments, the tubular segment 116 is between about 15 mm to about 20 mm in length and between about 6 mm to about 8 mm in diameter. For example, in one embodiment, the tubular segment 116 should be 6 mm in diameter if the procedural target is for the renal arteries, celiac axis and superior mesenteric arteries. For the larger supra-aortic branches, the tubular segment 116 may be larger e.g. 8 mm in diameter.

Figure 5:
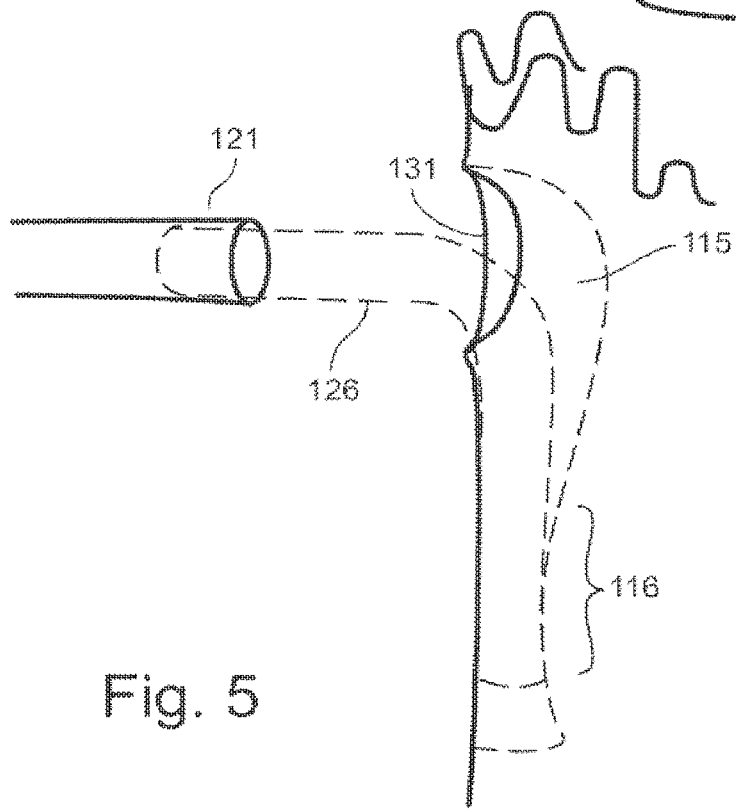
FIG. 5 shows a cannulation member with an endograft bridge to the renal artery.

The tubular segment 116 of the cannulation member 112 may be used to bridge the lumen 107 of the universal fenestrated endograft with a branch vessel 121, as is illustrated in FIG. 5. Referring now to FIG. 6, in one embodiment, the cannulation member is of proper dimension to allow a working catheter 122 to engage the ostium 123 of a branch vessel 124, introduce a guiding element 125, measure the distance between the tubular segment of the cannulation member (FIG. 6) and an initial length of a branch artery past the ostium, and place an secondary endograft (reference number 126 in FIG. 5) connecting the tubular segment of the cannulation member to the proximal end of the branch. In some embodiments, the initial length of the branch artery past the ostium to be measured is at between about 1.5 and 2 cm.

In some embodiments, implantation procedures are similar in many aspects but may differ in various aspects. For example, the procedure may be used to treat a juxta-renal aneurysm. For example, a universal fenestrated endograft with universal fenestrations for renal arteries and with an anterior scallop for the superior mesenteric artery (as shown in FIG. 7) is placed in the aorta, oriented by anterior radio-opaque marks and deployed at the optimal level to accommodate and receive the superior mesenteric artery ostium. Radio-opaque marks may also be placed at the ends and at the level of the external orifice. The universal fenestration may be positioned to receive the renal branches. At this point, a self expandable endograft may be released from the sheath releasing the partially constricting wire. Alternatively the partially constricting wire may be kept in position to achieve accurate positioning of the endograft. The internal orifice of the tubular segment of the cannulation member is directed caudally and the internal orifice is flared to facilitate cannulation. A catheter with an appropriate shape is introduced in the cannulation member through the internal orifice from below and the renal artery ostium is engaged and the artery is cannulated. A guiding element is introduced in the renal artery and a marked catheter used to measure the distance between the tubular segment of the cannulation member and 2 cm inside the renal artery. A secondary endograft is chosen and deployed to the site to function as a bridge between the cannulation member's tubular segment and the trunk of the renal artery as shown in FIG. 5. Balloon-expandable or self-expandable endografts may be used as shown in FIG. 12. After measuring the length of the tubular endograft needed to bridge the endograft and the branch, the endograft is advanced into the branch and released, the endograft is molded with a balloon and a final arteriogram performed.

The universal fenestrated endografts of the present invention may be used in any vessel. For example, in the case of the aorta, it may be applied to evaluate and/or treat juxta-renal aneurysms, abdominal aortic aneurysms, thoraco-abdominal aneurysms, aneurysms of the iliac arteries, and aneurysms of the aortic-arch.

As described above, a fenestration of the universal fenestrated endograft may be wide enough to cover or receive several arteries, such as the celiac axis, the superior mesenteric arteries and one or more renal arteries. Furthermore, the shape and construction of the cannulation member may be adjusted according to the number, profile, etc. of the arteries are being treated.

The universal fenestrated endografts of the present invention may comprise one or more cannulation members that further comprise one or more chambers within the tubular segments of the cannulation members. In one embodiment, the tubular segment of the cannulation member may comprise multiple chambers extending longitudinally through the tubular segment to the internal orifice. For example, as shown in FIGS. 14 and 15, if two branch arteries are covered, two chambers 127 and 128 may be constructed in the cannulation member 112 for cannulation of the specific branch artery target. As described previously, the internal orifices of cannulation members may be directed caudally (as depicted in FIG. 3) or cranially (as depicted in FIG. 18).

Figure 3B:
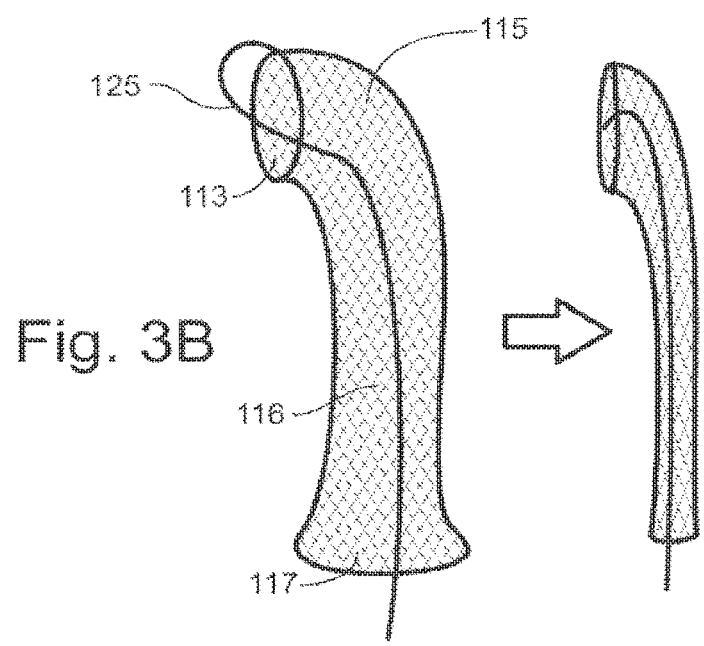
Figure 10A:
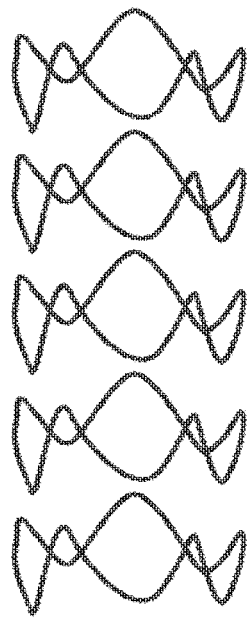
FIGS. 10A-B shows a one piece cannulation member and main body.
Figure 10B:
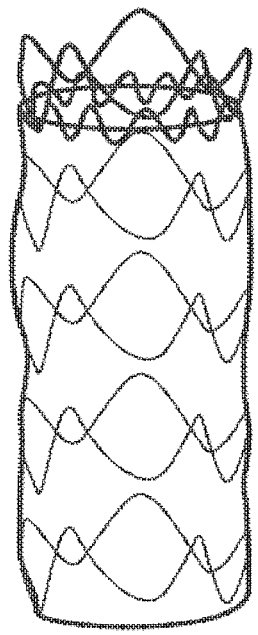

In some embodiments, (for example, as shown in FIG. 3B), the cannulation member may be braided or may comprise a zigzag construction to facilitate constriction of the universal fenestrated endograft with the cannulation member and delivery to a target vessel area and also to maintain integrity of form, shape, and profile once delivered to the target and expanded. In some embodiments, a cannulation member 112 may comprise a metal component which may be a continuation of the metal in the main universal fenestrated endograft as shown in FIGS. 10A and 10B. The cannulation member may be braided, attached to the edge of the fenestration and constricted for delivery (as shown in FIGS. 3 and 11) and/or may be malleable and constricted over a low profile balloon (as shown in FIG. 12). A metal component used in this manner may comprise a skeleton, frame, or lattice that substantially forms the shape of the cannulation member 112. The metal component may be covered by, for example, Dacron, ePTFE, or the like. It will be recognized that the external orifice 113 may also contain the metal component. In this manner, the external orifice's shape may be substantially preserved allowing instrumentation to progress through with little concern of collapse.

Figure 13A:
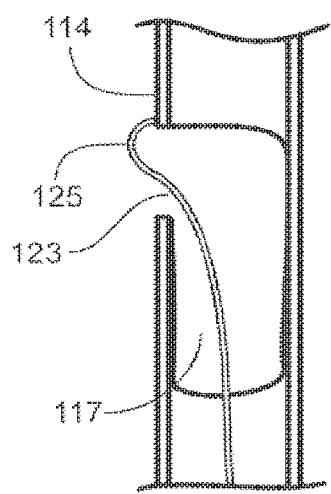
FIGS. 13A-B shows a guiding element engaged to the outside of the universal fenestrated endograft, entering through a lateral fenestration into a cannulation member, into the lumen of the endograft and exiting from an orifice of the valve of the sheath.
Figure 13B:
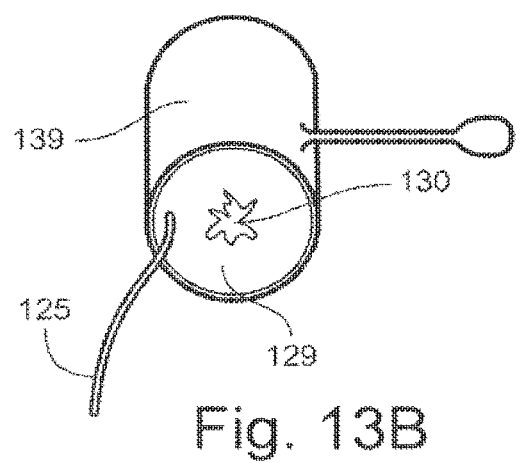

In some embodiments, the cannulation member of the present invention may further comprise a flared internal orifice 117 located at the end of the tubular segment as shown in FIG. 2. As shown in FIGS. 3B and 13A, the cannulation member 112 may additionally comprise a guiding element 125 attached to the cannulation member 112, for example, at the rim of the external orifice or universal fenestration. Referring to FIG. 13A-B, the guiding member 125 may extend through the external orifice 113, into the cavity 115 of the cannulation member, through the tubular segment 116, and out the internal orifice 117. The guiding element 129 may then follow inside the introducing sheath 129 and leaving from the valve 130 of the sheath or from an orifice made in the valve (as shown in FIG. 13B). In one embodiment, the guiding element 125 may be a thread or a guiding element. In similar manner, the cannulation member may contain a balloon exiting from the internal orifice of the cannulation member in the valve of the sheath.

The universal fenestrated endograft 100 will be suitable for passage of guiding elements, balloons, or other endovascular means of manipulation. It may also serve as a scaffold for the placement of devices meant to access tributaries and/or provide a conduit to them. It may serve as a scaffold for other endovascular graft materials or prostheses to perform roles of reinforcement or provide further competence of graft sections between intervening tributaries.

The universal fenestrated endograft 100 may be introduced over a catheter into an abdominal aortic aneurysm in a patient's aorta, for example. The universal fenestrated endograft 100 is preferably fixed in a normal part of aorta proximal to the section to be repaired or excluded. For example, fixation may be in the lower thoracic aorta for all abdominal pathology and proximal to the innominate artery for the thoracic pathology, although fixation can be placed at any normal diameter aorta with suitable mural morphology for the fixation technique. The proximal or upstream end of the universal fenestrated endograft 100 may be placed proximal or superior to any or all of the renal, hepatic and mesenteric arteries when appropriate.

The universal fenestrated endograft and the cannulation member may be self-expanding or it may be balloon expandable, or a combination of the two techniques may be used.

Referring now to FIGS. 3A-B, various embodiments of the invention are shown comprising a main universal fenestrated endograft 100 comprising a cannulating member 112. The cannulating member 112 shown within the universal fenestrated endograft 100 illustrated in FIG. 3A comprises a external orifice 113, which in this embodiment is the same size as the universal fenestration, a rim 114, a cavity 115, a tubular segment 116, and an internal orifice 117. Internal orifice 117 may be straight, tapered or flared as shown in the embodiment depicted in FIG. 2 and FIG. 3A. Preferably, the internal orifice 117 is flared to facilitate entry of instruments such as catheters into the cannulating member facilitating entry into and through the branch vessels.

The embodiment shown in FIG. 3B shows a cannulation member 112 with a guiding element 125 extending from the external orifice 113 and through cavity 115, tubular segment 116 and out internal orifice 117. FIG. 3B shows an embodiment of cannulation member 112 in an expanded and collapsed or constricted state. The cannulation member 112 shown in FIGS. 3A-B and FIGS. 11A-B is of a braided construction facilitating constriction of the cannulation member.

Figure 4:
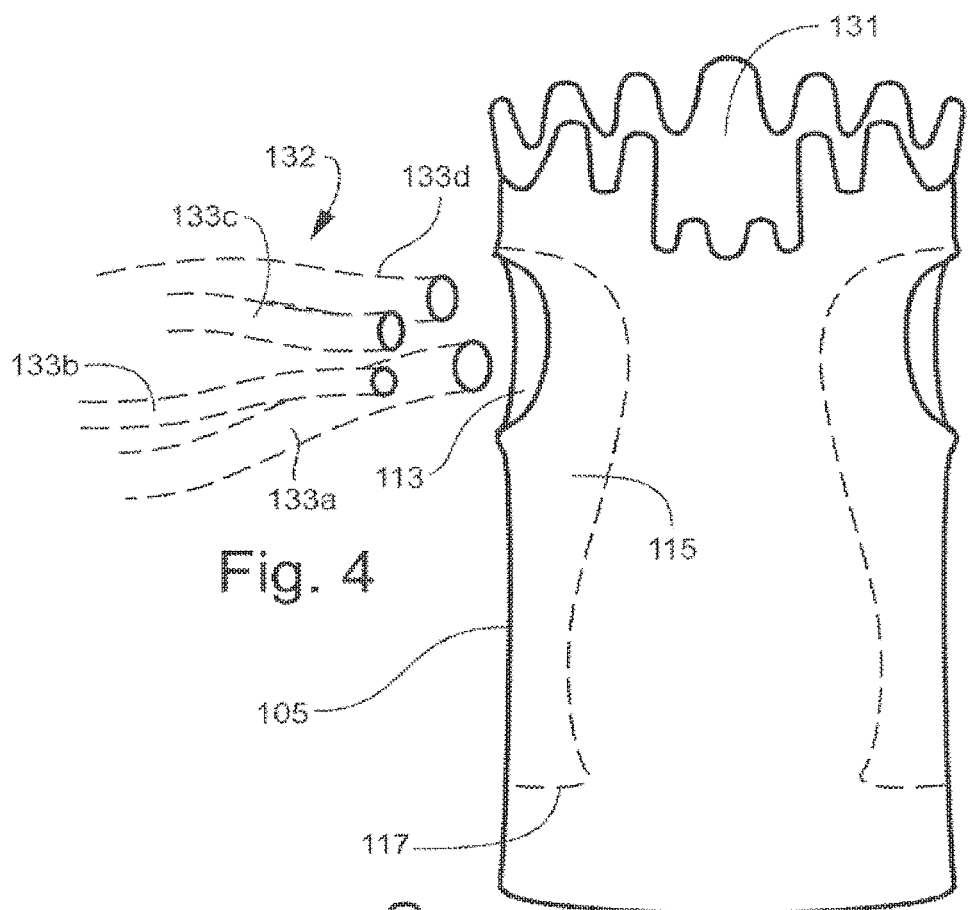
FIG. 4 shows a cranial segment of a universal fenestrated endograft depicting a scallop for the superior mesenteric artery and a cannulation member for renal artery coverage.

Referring now to FIG. 4, a cranial segment of an embodiment of the universal fenestrated endograft of the present invention is shown. Depicted in FIG. 4 is a scallop 131 for the superior mesenteric artery (SMA), as well as a right renal artery 132 in various positions with ostia 133 a, b, c, d exposed to view. In this example, an external orifice 113 of a cannulation member 112 is positioned within a first wall 105 of the main universal fenestrated endograft 100. Here, external orifice 113 is sufficiently large to accommodate connectivity with renal artery 132 at various positions and angles of approach. FIG. 4 also shows a cannulation member 112 with cavity 115 and internal orifice 117 opening into the lumen of main universal fenestrated endograft 100.

Referring now to FIG. 5, an embodiment of the present invention illustrating a cannulation member 112 connection to the renal artery 121 is shown. In this embodiment, renal artery 121 is connected via secondary endograft 126 to universal fenestrated endograft 100 positioned within the lumen of aorta. Secondary endograft 126 has been positioned using cannulation member 112 such that it extends from renal artery through external orifice 113 into cavity 115 and down tubular segment 116. In this Figure the renal artery is depicted for illustration purposes as separate and disconnected from the endograft 100, but it will be recognized by those of ordinary skill in the art that the renal artery during actual procedural conditions is connected to the aorta and the endograft 100.

Referring now to FIG. 6, an example of the method used to place secondary endograft 126 illustrated in FIG. 5 is shown. In this Figure, a catheter 122 and guiding element 125 is inserted into the flared internal orifice 117 of cannulation member 112 and extends through tubular segment 116, external orifice 113, and renal artery ostium 123. The markings on catheter 122 are used to measure the distance between tubular segment 116 and trunk of the renal artery branch. This measurement is used to guide deposit of the secondary endograft bridge shown in FIG. 5. In this Figure the renal artery is depicted for illustration purposes as separate and disconnected from the endograft 100, but it will be recognized by those of ordinary skill in the art that the renal artery during actual procedural conditions is connected to the aorta and the endograft 100. The renal artery is connected to endograft 100 once the secondary endograft 126 is deployed between the tubular segment and the initial segment of the branch artery.

Referring now to FIG. 7 an upper segment of a universal fenestrated endograft is shown. In this embodiment the intersection of the abdominal aorta, the superior mesenteric artery, and the left and right renal arteries is illustrated. A main universal fenestrated endograft 100 comprises a scallop 133 which is a larger fenestration within endograft 100 for connection with superior mesenteric artery. The endograft 100 is shown with two cannulation members 112a and 112b for connection with left and right renal arteries. FIG. 3 also shows an aortic aneurism under repair.

Fenestrated endografts are commonly inserted and positioned within a vessel in a constricted form. Once adjusted to proper position, the ends of the endograft are released in sequential order and attached to the walls of the vessel. FIG. 1 illustrates an example of a main universal fenestrated endograft in partially constricted form and released/expanded form. The partially constricted endograft allows changes in orientation facilitating cannulation of the branches.

Figure 8:
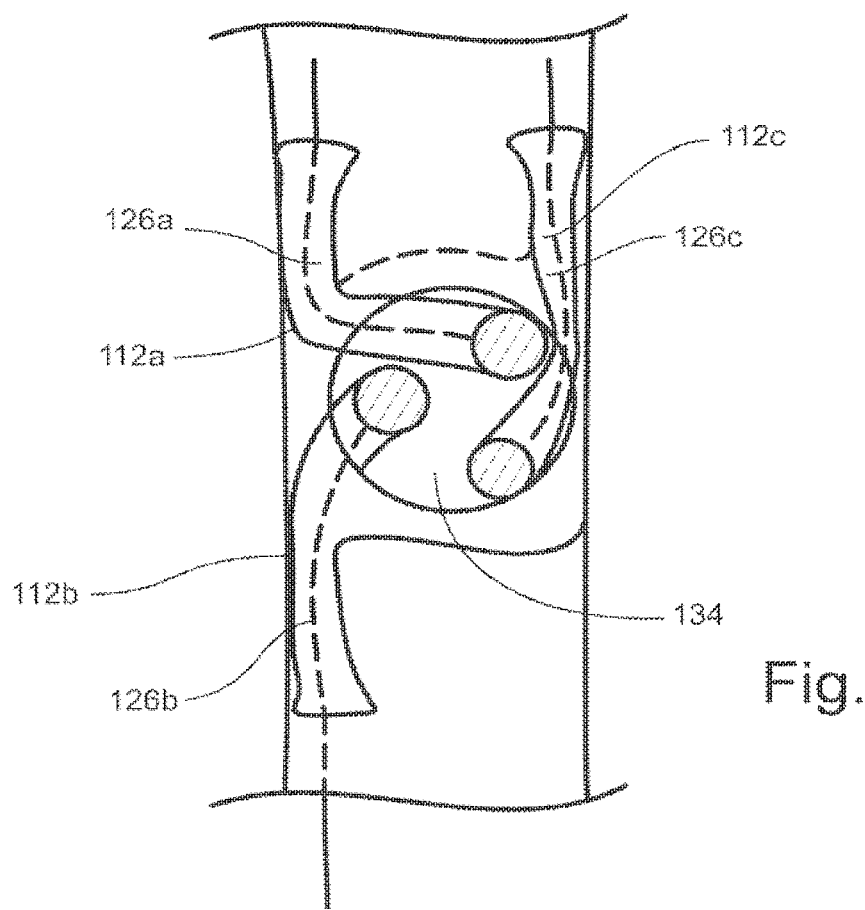
FIG. 8 shows universal fenestrated endograft with three independent cannulation members sharing a single external orifice and fenestration covering three branch vessels, the superior mesenteric artery (SMA), the celiac axis (CA) and the right renal artery.

FIG. 8 shows a universal fenestrated endograft 100 of the present invention comprising three independent cannulation members 112a, 112b, 112c extending from a single universal fenestration or orifice 134. In this embodiment, the three independent cannulation members pair up with the superior mesenteric artery (SMA), the celiac axis (CA) and the right renal artery. The embodiment illustrated in FIG. 8 shows three secondary endografts 126a, 126b, 126c that have been deposited to bridge with the SMA, CA, and right renal artery using the specific cannulation member for each artery.

Figures 9A, 9B:
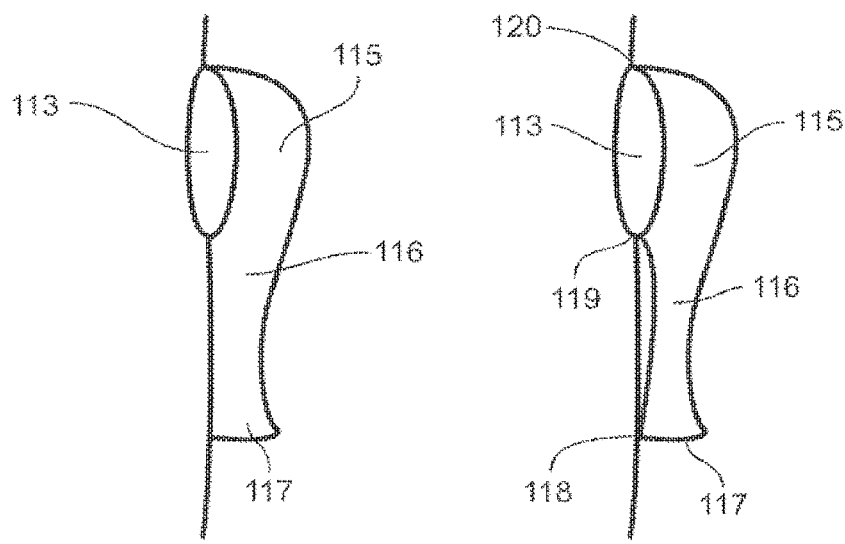
FIGS. 9A-B illustrates embodiments of how the cannulation member may engage the universal fenestrated endograft.

FIGS. 9A-B shows two embodiments of the cannulation member and how it engages to the universal fenestrated endograft 100. In one embodiment, the cannulation member 112 shares walls with the main endograft and, in the other embodiment, the cannulation member walls are independent of the walls of the main endograft except that the cannulation member may be attached at to the main endograft at attachments point 118, 119, 120. For example, the attachment point may be at the edge of the universal fenestration.

FIG. 10 illustrates that the universal fenestrated endograft and the cannulation member may be a one piece construction wherein the cannulation member forms a part of the main body of the universal fenestrated endograft.

Figure 11A:
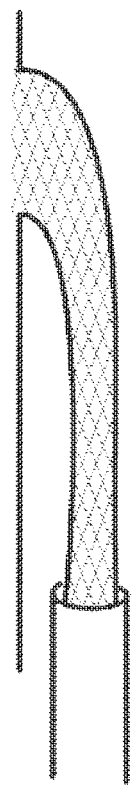
FIGS. 11A-B shows a braided cannulation member in constricted (FIG. 10A) and expanded (FIG. 10B) form.
Figure 11B:
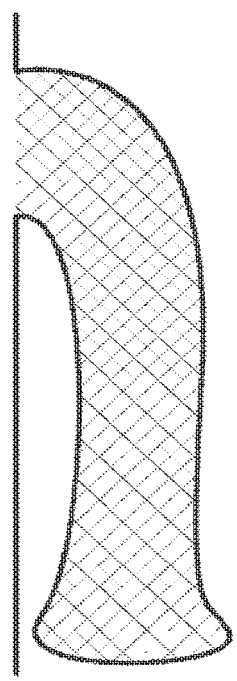

In another embodiment of the present invention, fenestrated endografts may comprise cannulation members that are braided as shown in FIGS. 11A-B and FIG. 2B to facilitate constriction or compression and delivery of the universal fenestrated endograft to the target site. FIG. 11 shows a braided cannulation member design in compressed (FIG. 11A) and expanded (FIG. 11B) form.

Figure 12A:
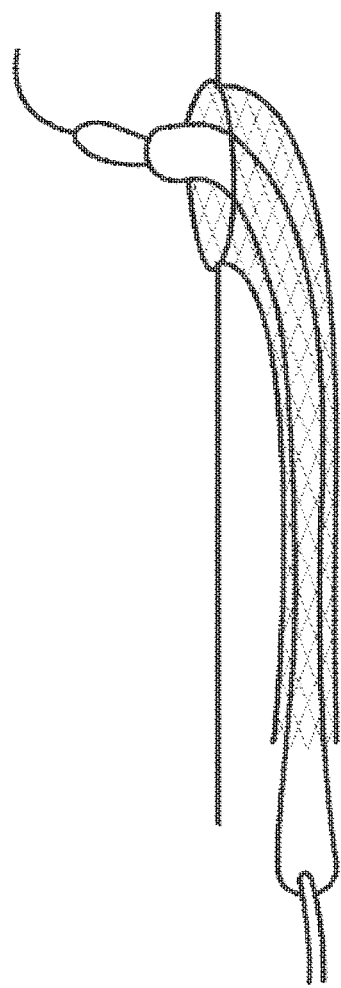
FIGS. 12A-B shows a malleable cannulation member comprising a balloon with balloon contracted (FIG. 9A) and expanded (FIG. 9B).
Figure 12B:
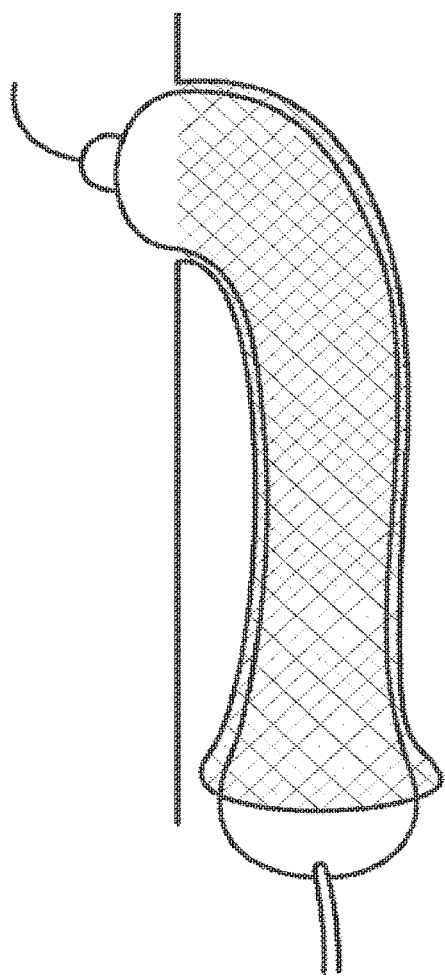

In another embodiment of the present invention, the fenestrated endografts may comprise cannulation members that are malleable, such that they may fit securely over an object of various sizes and profiles. For example, FIG. 12 shows a malleable cannulation member of the present invention covering a balloon. The malleable cannulation member may be compressed (FIG. 12A) or expanded (FIG. 12B) depending on the needs, size, or profile of the object. In one embodiment, a malleable cannulation member is initially compressed for deployment, and once the universal fenestrated endograft is expanded, a balloon is inflated and the cannulation member expanded.

FIGS. 14A-F show an embodiment of the present invention depicting the universal fenestrated endograft positioned within the aortic arch. In this embodiment, external orifice 113 is large enough and positioned to accommodate two or more supra-aortic branches. For example, in FIGS. 14A-C, the external orifice 113 receives two supra-aortic branches, specifically the innominate 135 and left carotid 136 arteries. In this embodiment, cannulation member 112 is constructed with two chambers, 127 and 128 respectively, one for receipt of a secondary endograft 126a for an innominate arterial bridge and the other for receipt of a secondary endograft 126b for a left carotid artery bridge. In this embodiment, the two chambers 127 and 128 are positioned in the tubular segment 116 of cannulation member 112.

Figure 15A:
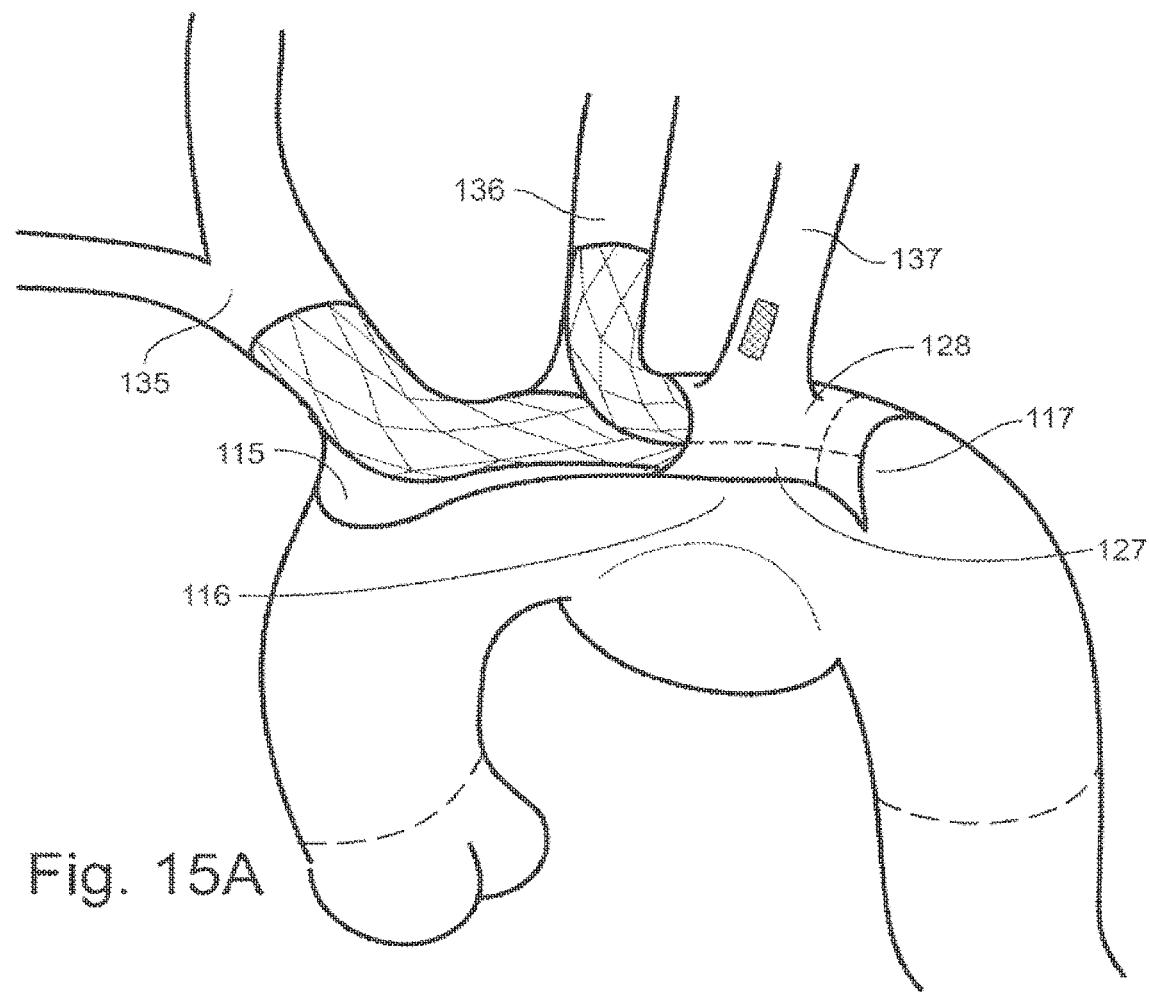
FIGS. 15A-B show one embodiment of the present invention depicting a universal fenestrated endograft connected with supra-aortic trunks.
Figure 15B:
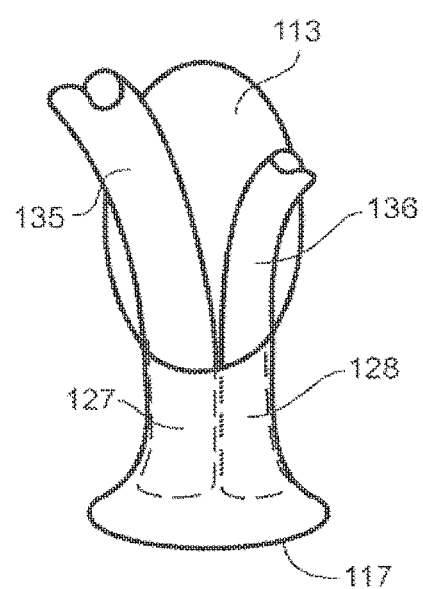

FIGS. 15A-B show an embodiment of the present invention depicting a universal fenestrated endograft connected with supra-aortic trunks. The embodiment illustrated in FIGS. 15A-B is similar to that of FIGS. 14A-F except that the subclavian artery 137 has been plugged to occlude blood flow. Alternatively, if the subclavian blood flow needs to be preserved, the universal fenestrated endograft of the present invention can be modified to cover it as well.

FIG. 16 shows an embodiment of the present invention depicting a universal fenestrated endograft 100 to common iliac artery aneurysms. In this embodiment, the universal fenestrated endograft 100 is bifurcated and positioned in the iliac arteries. The main endograft in this example comprises a long limb 138 extending to the external iliac artery 139 and a short tubular segment 140 with a big cannulation member 112 with a flared internal orifice 117 directed toward the hypogastric artery 141. FIG. 16 also shows a secondary endograft 126 connecting the tubular segment 140 of the cannulation member 112 with the hypogastric artery 141.

Figure 17A:
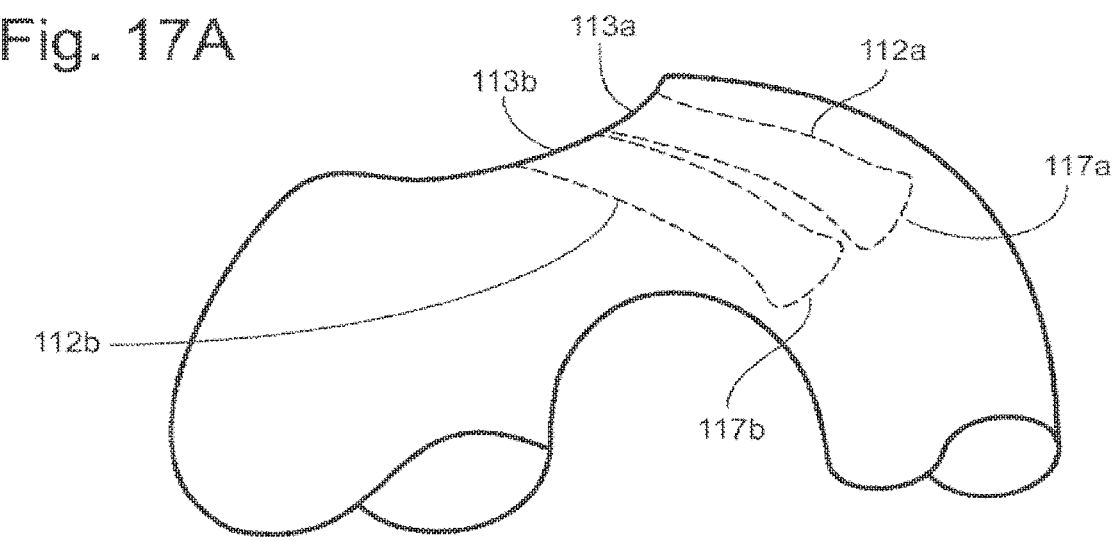
FIGS. 17A-B show different views of a universal fenestrated endograft for the aortic arch with preservation of the flow of the innominate and left carotid trunks.
Figure 17B:
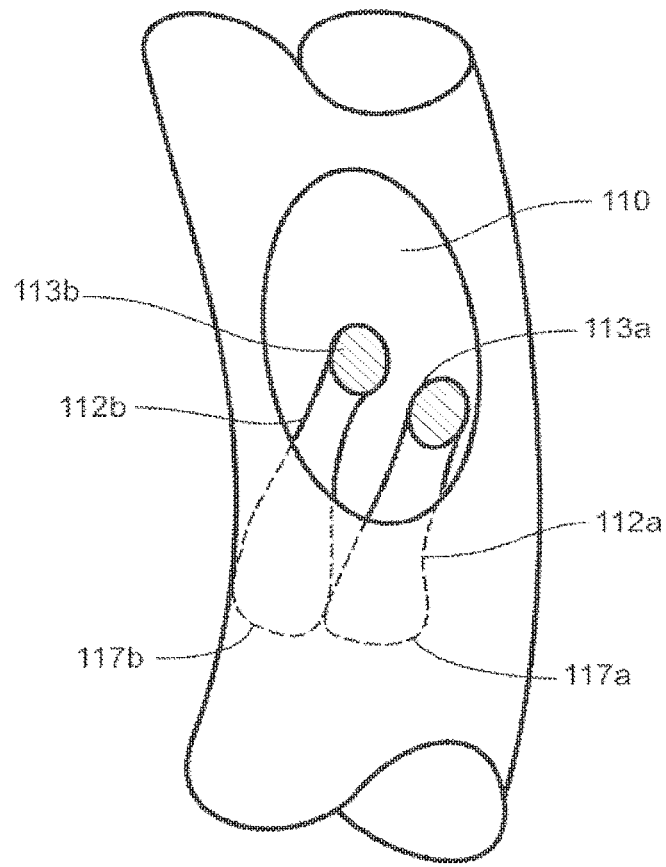

FIGS. 17A-B show an embodiment of the universal fenestrated endograft of the present invention for the aortic arch with preservation of the flow of the innominate and left carotid trunks. In this embodiment, there are two independent cannulation members 112a and 112b, one for the left carotid artery and one for the innominate trunk. In this embodiment, the cannulation members are obliquely angled to facilitate blood flow.

Figure 18A:
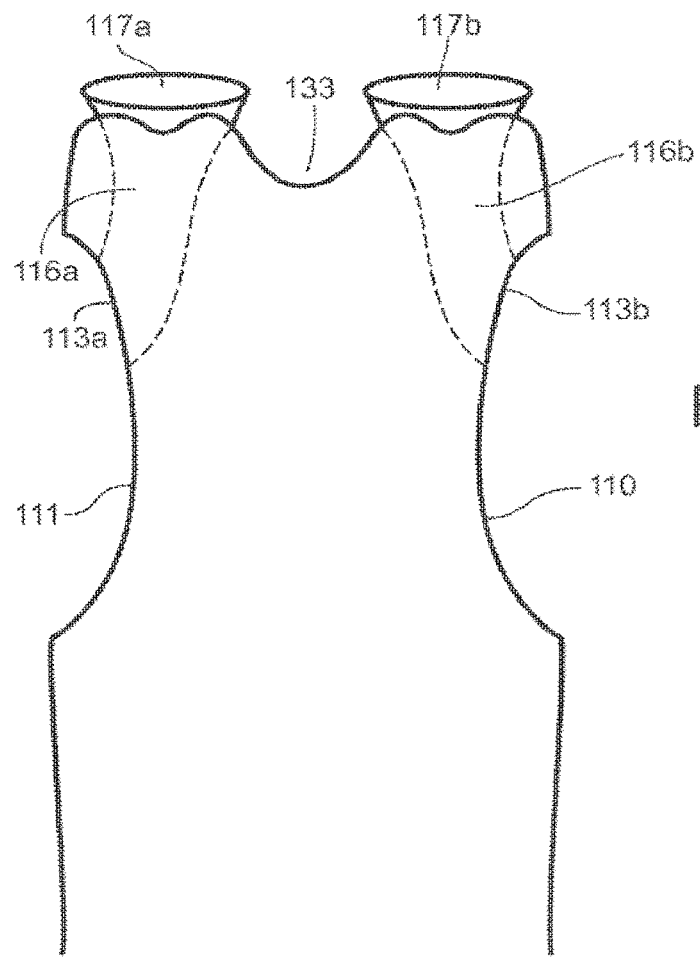
FIGS. 18A-B show different views of a universal fenestrated endograft for the juxta-renal aorta artery.
Figure 18B:
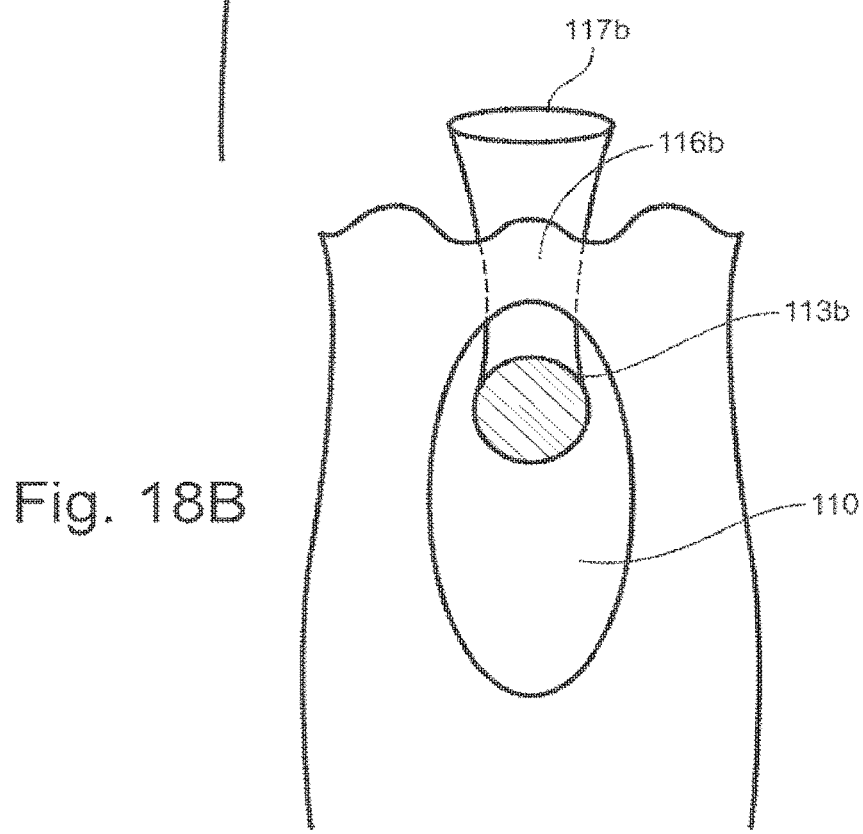

FIGS. 18A-B show an embodiment of the present invention depicting a universal fenestrated endograft for the juxta-renal artery. In this embodiment, the main universal fenestrated endograft 100 comprises an external orifice 113 which is designed to accommodate renal arteries extending from the abdominal aorta, a cannulation member 112 with a tubular segment 116, and an internal orifice 117. Also, shown in this embodiment is a scallop 134 for entry of the superior mesenteric artery and connection to the lumen of the main universal fenestrated endograft 100. In this embodiment, the cannulation members 112a and 112b are directed cranially for top entry.

Figure 19A:
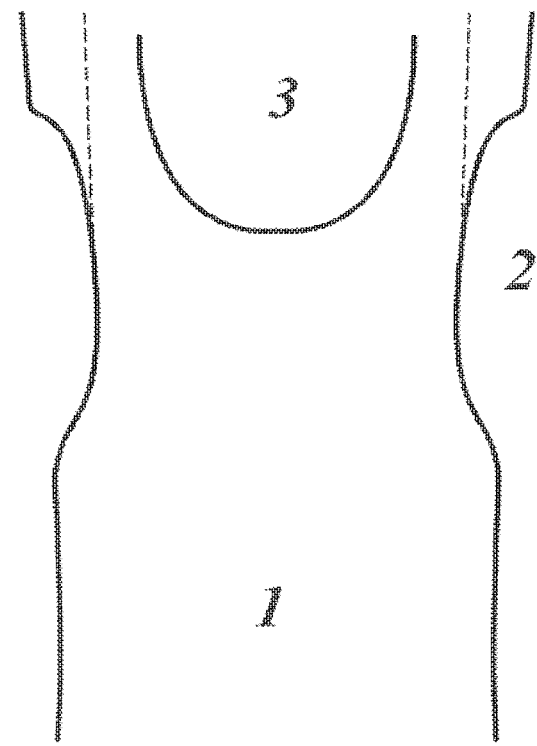
FIGS. 19A-B show different views a universal fenestrated endograft for the juxta-renal aorta artery with cylinders for the celiac trunk, superior mesenteric and renal arteries.
Figure 19B:
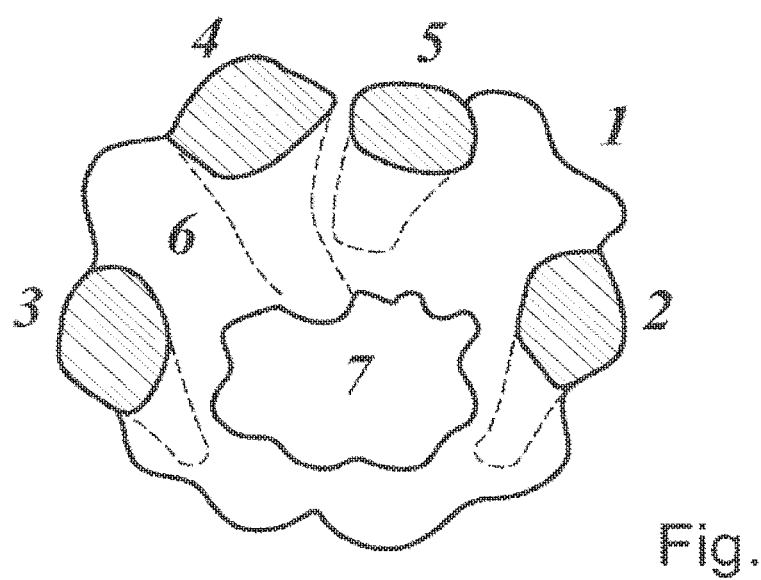

FIGS. 19A-B show an embodiment of the present invention depicting a universal fenestrated endograft for the juxta-renal artery with three cannulation members for the celiac trunk, superior mesenteric and renal arteries.

The present invention additionally relates to universal branched endografts. In some embodiments, a universal branched endograft device includes a main tubular body/cylinder. In one embodiment, the main tubular body/cylinder is about 6 cm in length. The main tubular body/cylinder may have a variable diameter. A second cylinder/lumen may be placed inside the main cylinder. In one embodiment, the second cylinder/lumen is about 15 cm in length and about 18 mm in diameter. Inside the main cylinder there may be one or more smaller branch lumens/cylinders following the same longitudinal axis as the main cylinder. In one embodiment, the branch lumens/cylinders are the same diameter. In a preferred embodiment, however, the branch lumens/cylinders are of different diameters. For example, in one embodiment of a universal branched endograft comprising four branch lumens/cylinders, two are 6 mm in diameter and the remaining two are 8 mm in diameter. The four small cylinders are placed radially along the circumference of the main cylinder of the 15 cm long cylinder.

In some embodiments, diameters of the branches are made standard as well as lengths, with the diameter of the main cylinder being a selectable variable for use in particular anatomy.

In some embodiments, a proximal segment has no independent wall and shares the outer wall of the main and short cylinders or, in alternative embodiments, just has a fabric wall. In such embodiments, the outer walls of the short segments together with the inner wall of the main endograft create a channel for the aortic extension.

In some embodiments, an inner surface of the short and 15 cm long cylinders have the metal stent-like skeleton. An endograft couples to the skeleton, and is locked into place. The metal and fabric are kept together with sutures or different glues. A membrane can be used to put together the metal and the fabric. In an alternative embodiment of the short cylinder, the wall is solely fabric and has two metallic rings at the ends to maintain patency.

The wall of the cylinders can be, in general, a combination of fabric and metal to make up the standard wall of an endograft. The metal can be nitinol, nobalt-chromium or stainless steel or any suitable material having similar characteristics. Metal barbs can be part of the metal skeleton and protrude outside the main cylinder. Radio-opaque marks can be placed anteriorly and on the left lower quadrant for orientation.

In some embodiments, cylinders can be placed inside the main cylinder and the interstices filled with compressible texturized fabric. The fabric can be made of polyester or ePTFE. But generally, any membrane or fabric-like biocompatible, non-absorbable material can be used. Alternatively, no interstices may be created and all or some walls may be shared among the cylinders.

As mentioned above, some embodiments, the different cylinders can be independent of one another or they can share walls with adjacent cylinder(s). In the case of independent walls, spaces among the different components can be filled with soft and compressible fabric, which seal the interstices. Alternatively, the four small cylinders are joined and are attached along the periphery of the main cylinder cavity. The remaining volume of the cavity, after attaching the joined four cylinders, constitutes the cavity of the 15 cm long cylinder which in the initial 6 cm of length share walls with the inner main cylinder and the outer surface of the joined four small cylinders. Accordingly, the upper part of the 15 cm long cylinder uses the outer wall of the small and main cylinders. At the caudal edge of the main endograft, the cavity continues with the wall of the 15 cm long cylinder that extends cylindrically for the remaining 9 cm.

In some embodiments, walls of the small cylinders are solely constructed of fabric, however, with the incorporation of a row of metal at both ends of the cylinders to keep the cavity open.

In some embodiments, the 15 cm long cylinder is configured as 9 cm of the main cylinder, with its wall being solely fabric for the initial 6 cm and fabric with metal in the following 9 cm. Alternatively, the upper part of the 15 cm long cylinder shares a wall in the initial 4 cm and in the last 2 cm has its own fabric wall. The proximal 6 cm long segment can have an irregular shape which is the volume of the cavity of the main cylinder minus the area occupied by the short cylinders. The proximal cavity of the 15 cm long cylinder continues with the now circular section tube with metal reinforcing the fabric.

The small cylinders are kept open with a stent-like metal skeleton. Metal in the small cylinders in the form of "zigs" are located in the inner surface of the tube in order to interact with the metal skeleton of the connecting tube endograft which lies outside. Zigs of the small cylinder and connecting endograft (tube) match with each other and lock the connection between them. Eventually small cylinders are fabricated with fabric alone and two rings are applied at the ends to keep them open.

In some embodiments, the diameter of the universal branched endograft may be selected by adding 15% of the diameter of the normal aorta above the aneurysm.

Implanting procedures of the universal branched endografts may generally comprise the following steps. Implantation of the universal branched endograft may be performed from the common femoral artery percutaneously or through a cut down. The delivery system containing the universal branched endograft is advanced over a guiding element to reach the area of deployment proximal to the target, e.g. aneurysm. Anterior radio-opaque marks or other technique may assist to orient the device properly, and after checking the right orientation, the universal branched endograft is deployed. Once deployed to the desired position, the channels may be cannulated and the branches cannulated one by one. A catheter and guiding element may locate the lumen of the visceral branches. Distance is calculated using marked catheters or other technique and an appropriate secondary endograft selected according to factors such as the distance and diameter of the target branches. Guided by guiding element, each secondary endograft may be deployed and molded with a balloon. In one embodiment, the initial 15 mm of the target branch is covered by the secondary endograft. Initial placement of the universal endograft may be carried out from the femoral artery. Cannulation of the channels and branches may be carried out from the upper extremities.

For example, in one embodiment, a guiding element is inserted from the femoral artery to the thoracic aortic lumen using the wire as a guide. A sheath containing the endograft is advanced up to the desired position and deployed using radio-opaque marks as references. Once deployed, the branches are cannulated from above and catheters introduced into the visceral branches. Guided by guiding elements, secondary endografts are deployed bridging the universal branched endograft and the aortic branches.

In some embodiments, each small cylinder may be cannulated and extended via a tube endograft inside the visceral branches. The medially located small cylinders may be used to extend into the celiac axis and the superior mesenteric arteries. The lateral small cylinders may be used to extend into both renal arteries.

In some embodiments, the main cylinder may be fixed to the aortic wall by friction and by active fixation defined by barbs, which are part of the metallic component of the endograft.

In some embodiments, a non-compliant balloon may be used to insure good apposition of the connecting endografts and the short cylinders and the visceral arteries. Additional bare stents can be used to secure apposition of the segments connected.

In some embodiments, a final arteriogram may be performed to rule out any endoleaks.

Figure 20:
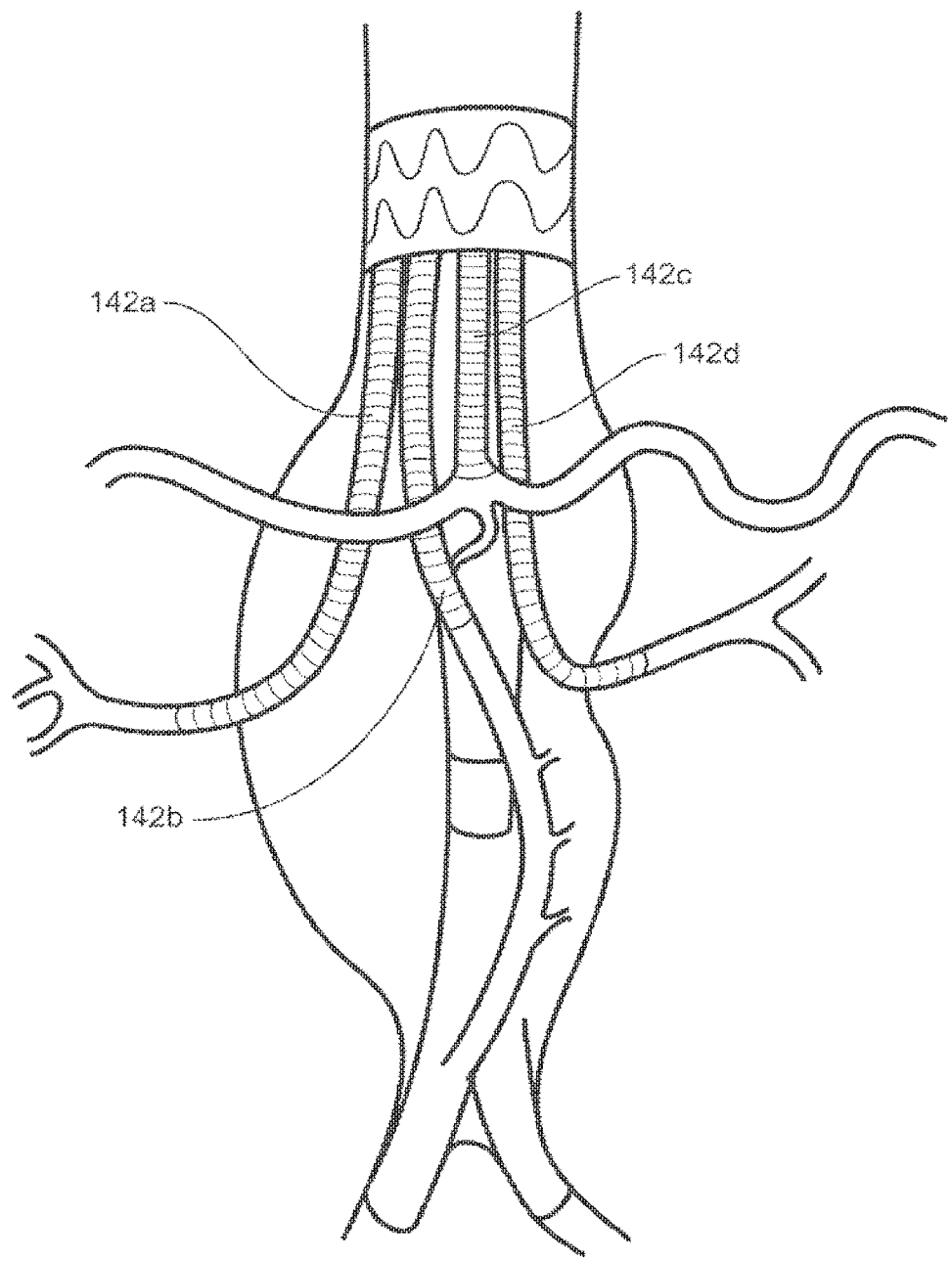
FIG. 20 shows an embodiment of a universal branched endograft of the present invention with four endograft extensions to the left renal, celiac, superior mesenteric, and right renal arterial branches.

Referring now to FIG. 20, an embodiment of the universal branched endograft of the present invention is shown. In this embodiment, the universal branched endograft has four endograft extensions 142a, 142b, 142c, 142d from four adjacent cylinders (not shown). In this embodiment, the four endograft extensions are to the left renal, celiac, superior mesenteric, and right renal arteries respectively.

Figure 21A:
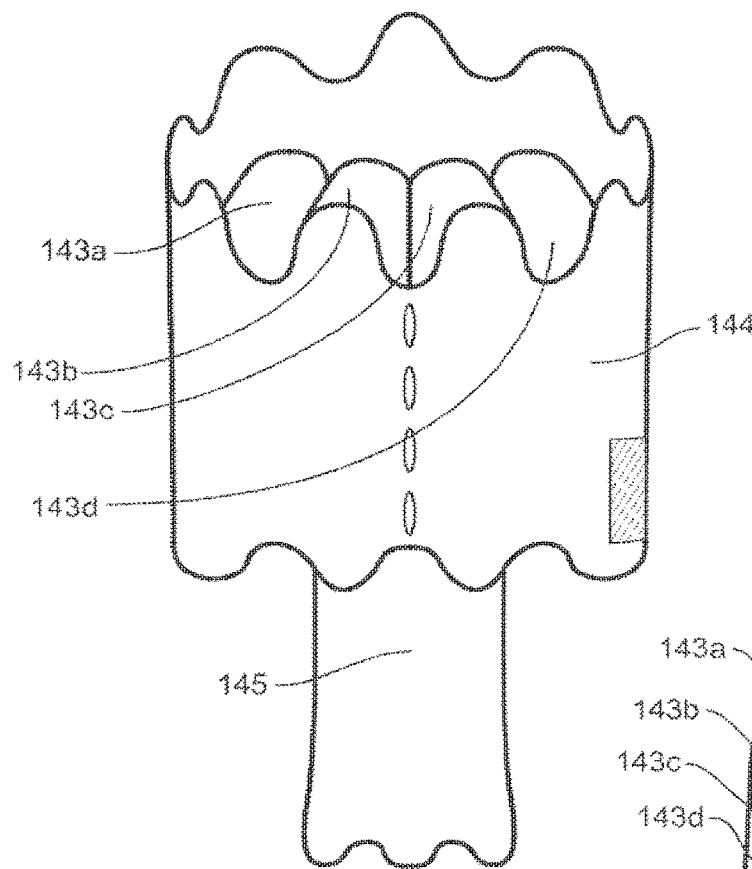
FIGS. 21A-C shows an embodiment of the universal branched endograft of the present invention.
Figure 21B:
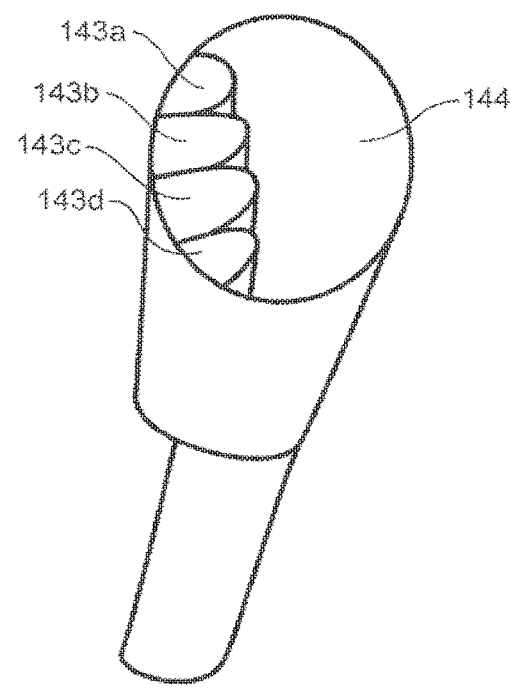
Figure 21C:
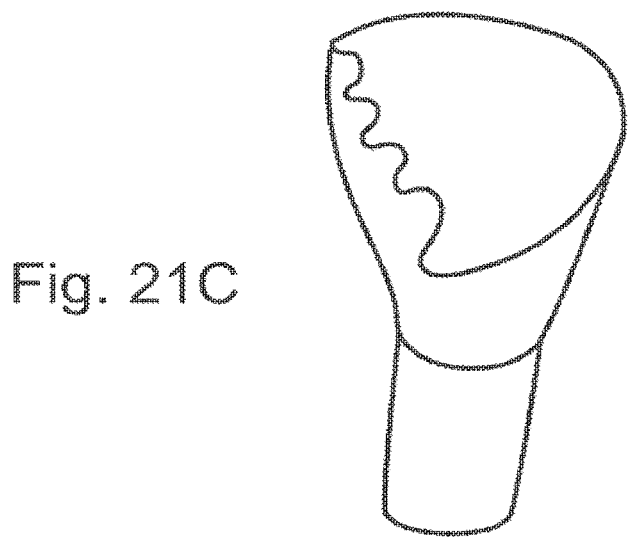

Referring now to FIG. 21, an embodiment of the universal branched endograft of the present invention is shown. The four adjacent cylinders 143a, 143b, 143c, and 143d are shown within the main tubular body/cylinder 144 and placed radially along the circumference of the main cylinder. A second cylinder/lumen 145 is shown extending from the main cylinder.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof. For example, although specific examples have been described for treatment of thoracic and abdominal aortic aneurysms, the apparatus and methods described herein are also applicable to other vessels of the body, including other arteries, veins and other body passages. It should be recognized by persons of ordinary skill that features of the universal fenestrated endografts described herein may be combined with features of the universal branched endografts described herein and vice versa. For example, the universal endografts of the present invention may share various material, dimensional, and structural components. Furthermore, fenestrated endografts may be branched and vice versa.

What is claimed is:

1. An endovascular graft comprising:
a body (101) extended along a longitudinal axis (102), the body being expandable and having a first end (103), a second end (104), and an interior passage (107), and an internal surface and external surface;
wherein the body (101) includes a first opening (108) and a second opening (109) in communication with the interior passage (107) at the first end (103) and the second end (104), the first opening and the second opening being substantially transverse to the longitudinal axis (102);
wherein the body (101) includes a universal fenestration (134) in communication with the interior passage (107) and between the first end (103) and the second end (104); and
three independent cannulation members (112a, 112b, 112c) extending from the universal lateral fenestration (134);
wherein each independent cannulation member (112a, 112b, 112c) engages an internal surface of the body (101) at an attachment point; and
wherein each independent cannulation member (112a, 112b, 112c) includes a first orifice and a second orifice defining a length therebetween, with the first and second orifice of each independent cannulation member disposed within the interior passage.

2. The endovascular graft of claim 1, wherein the cannulation members (112 a, 112b, 112c) comprise an external orifice (113) further comprising a rim (114), a cavity (115), a tubular segment (116), and an internal orifice (117).

3. The endovascular graft of claim 1, wherein the cannulation members (112 a, 112b, 112c) are funnel-shaped.

4. The endovascular graft of claim 1, wherein the cannulation members (112 a, 112b, 112c) comprise an external orifice (113) that is between about 3 cm and about 7 cm in diameter.

5. The endovascular graft of claim 1, wherein the cannulation members (112 a, 112b, 112c) comprise an external orifice (113) that is about 4 cm in diameter.

6. The endovascular graft of claim 1, wherein the cannulation members (112 a, 112b, 112c) comprise an internal orifice (117) that is flared to facilitate cannulation.

7. The endovascular graft of claim 1, wherein the cannulation members (112 a, 112b, 112c) comprise a tubular segment (116) that is between about 6 mm and about 8 mm in diameter.

8. The endovascular graft of claim 1, wherein the cannulation members (112 a, 112b, 112c) comprise a tubular segment (116) that is between about 15 mm and about 20 mm in length.

9. The endovascular graft of claim 1, wherein the cannulation members (112 a, 112b, 112c) comprise a metal constituent for substantially maintaining the dimensional profile of the cannulation member.

10. The endovascular graft of claim 1, wherein the cannulation members (112 a, 112b, 112c) have a longitudinal axis that is at an oblique angle to the longitudinal axis of the body.

11. The endovascular graft of claim 1, wherein the cannulation members (112 a, 112b, 112c) comprise a braided construction.

12. The endovascular device of claim 1, wherein two of the three independent cannulation members extends a first direction from the universal fenestration (134) and one of the three independent cannulation members extends in a direction opposite the first direction.

13. The endovascular graft of claim 1, further including three secondary endografts (126a, 126b, 126c) each extending through the universal fenestration (134) and within a lumen of each of the three cannulation members (112a, 112b, 112c).

14. The endovascular graft of claim 1, wherein the attachment point for at least one of the cannulation members (112a, 112b, 112c) is spaced from the universal fenestration (134).

15. The endovascular graft of claim 1, wherein at least one of the cannulation members (112a, 112b, 112c) share a wall in common with the internal surface of the body (101).

16. The endovascular graft of claim 1, wherein each cannulation member (112a, 112b, 112c) engages an internal surface of the body (101) with each cannulation member (112a, 112b, 112c) attached to an edge of the universal lateral fenestration (134) at one or more attachment points.

* * * * *